United States Patent
Aston et al.

(10) Patent No.: US 8,252,818 B2
(45) Date of Patent: *Aug. 28, 2012

(54) NICOTINAMIDE DERIVATIVES USEFUL AS P38 INHIBITORS

(75) Inventors: Nicola Mary Aston, Stevenage (GB); Paul Bamborough, Stevenage (GB); Ann Louise Walker, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 65 days.

This patent is subject to a terminal disclaimer.

(21) Appl. No.: 12/713,433

(22) Filed: Feb. 26, 2010

(65) Prior Publication Data

US 2010/0215652 A1   Aug. 26, 2010

Related U.S. Application Data

(63) Continuation of application No. 11/462,851, filed on Aug. 7, 2006, now Pat. No. 7,709,506, which is a continuation of application No. 10/503,968, filed as application No. PCT/GB03/00554 on Feb. 10, 2003, now Pat. No. 7,125,898.

(30) Foreign Application Priority Data

Feb. 12, 2002 (GB) .................................. 0203301.7
Oct. 31, 2002 (GB) .................................. 0225385.4

(51) Int. Cl.
*A61K 31/44* (2006.01)
*C07D 213/02* (2006.01)

(52) U.S. Cl. ........................................ 514/355; 546/316
(58) Field of Classification Search .................. None
See application file for complete search history.

(56) References Cited

U.S. PATENT DOCUMENTS

| | | | |
|---|---|---|---|
| 4,200,750 A | 4/1980 | Warner et al. | |
| 4,968,804 A | 11/1990 | Stanck et al. | |
| 5,064,832 A | 11/1991 | Stanek et al. | 514/256 |
| 5,236,934 A | 8/1993 | VanAtten | |
| 5,246,943 A | 9/1993 | Blankley et al. | |
| 5,521,213 A | 5/1996 | Prasit et al. | |
| 5,534,518 A | 7/1996 | Henrie et al. | |
| 5,658,903 A | 8/1997 | Adams et al. | |
| 5,858,995 A | 1/1999 | Kawai et al. | |
| 5,877,190 A | 3/1999 | Dhainaut et al. | |
| 5,932,576 A | 8/1999 | Anantanarayan et al. | |
| 5,945,418 A | 8/1999 | Bemis et al. | |
| 5,977,103 A | 11/1999 | Adams et al. | |
| 6,060,491 A | 5/2000 | Pruitt et al. | |
| 6,080,767 A | 6/2000 | Klein et al. | |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,174,887 B1 | 1/2001 | Haruta et al. | |
| 6,251,914 B1 | 6/2001 | Adams et al. | |
| 6,277,989 B1 | 8/2001 | Chakravarty et al. | |
| 6,323,227 B1 | 11/2001 | Klein et al. | |
| 6,392,047 B1 | 5/2002 | Geissler et al. | |
| 6,399,627 B1 | 6/2002 | Song et al. | |
| 6,420,561 B1 | 7/2002 | Haruta et al. | 544/399 |
| 6,436,925 B1 | 8/2002 | Lubisch et al. | |
| 6,448,257 B1 | 9/2002 | Mavunkel et al. | 514/292 |
| 6,451,794 B1 | 9/2002 | Beswick et al. | |
| 6,498,166 B1 | 12/2002 | Campbell et al. | |
| 6,509,361 B1 | 1/2003 | Weier et al. | |
| 6,509,363 B2 | 1/2003 | Salituro et al. | |
| 6,545,054 B1 | 4/2003 | Song et al. | 514/603 |
| 6,576,632 B1 | 6/2003 | Goldstein et al. | |
| 6,579,872 B1 | 6/2003 | Brown et al. | 514/235.5 |
| 6,605,625 B2 | 8/2003 | Peukert et al. | |
| 6,638,980 B1 | 10/2003 | Su et al. | |
| 6,696,464 B2 | 2/2004 | McClure et al. | 514/303 |
| 6,699,994 B1 | 3/2004 | Babu et al. | |
| 6,774,127 B2 | 8/2004 | Adams et al. | |
| 6,794,377 B2 | 9/2004 | Peukert et al. | |
| 6,821,965 B1 | 11/2004 | Brown et al. | 514/217.05 |

(Continued)

FOREIGN PATENT DOCUMENTS

EP   0 533 266   9/1992

(Continued)

OTHER PUBLICATIONS

U.S. Appl. No. 10/492,714, filed Apr. 15, 2004, Angell et al.

(Continued)

*Primary Examiner* — Zinna Northington Davis
(74) *Attorney, Agent, or Firm* — James P. Riek

(57) ABSTRACT

Compounds of formula (I):

$$
\text{(I)}
$$

are inhibitors of p38 kinase and are useful in the treatment of conditions or disease states mediated by p38 kinase activity or mediated by cytokines produced by the activity of p38.

2 Claims, No Drawings

U.S. PATENT DOCUMENTS

| | | | |
|---|---|---|---|
| 6,855,719 B1 | 2/2005 | Thomas et al. | |
| 6,867,209 B1 | 3/2005 | Mavunkel et al. | 524/253 |
| 6,924,392 B2 | 8/2005 | Peukert et al. | 564/155 |
| 6,936,719 B2 | 8/2005 | Babu et al. | 546/323 |
| 6,956,037 B2 | 10/2005 | Brown et al. | 514/235.5 |
| 7,125,898 B2 | 10/2006 | Aston | |
| 7,151,118 B2 | 12/2006 | Angell et al. | |
| 7,166,597 B2 | 1/2007 | Alberti et al. | |
| 7,166,623 B2 | 1/2007 | Angell et al. | |
| 7,183,297 B2 | 2/2007 | Angell et al. | |
| 7,208,629 B2 | 4/2007 | Angell et al. | |
| 7,271,289 B2 | 9/2007 | Aston | |
| 7,309,800 B2 | 12/2007 | Angell et al. | |
| 7,384,963 B2 | 6/2008 | Angell et al. | |
| 7,396,843 B2 | 7/2008 | Angell et al. | |
| 7,425,555 B2 | 9/2008 | Angell et al. | |
| 7,432,289 B2 | 10/2008 | Angell et al. | |
| 7,514,456 B2 | 4/2009 | Aston | |
| 7,572,790 B2 | 8/2009 | Aston et al. | |
| 7,626,055 B2 | 12/2009 | Aston | |
| 7,642,276 B2 | 1/2010 | Angell et al. | |
| 7,687,532 B2 | 3/2010 | Campos et al. | |
| 7,709,506 B2 | 5/2010 | Aston | |
| 7,838,540 B2 | 11/2010 | Walker | |
| 2001/0011135 A1 | 8/2001 | Reidl et al. | |
| 2003/0055088 A1 | 3/2003 | Shao et al. | |
| 2003/0100756 A1 | 5/2003 | Adams et al. | |
| 2003/0139605 A1 | 7/2003 | Riedl et al. | 546/291 |
| 2003/0225089 A1 | 12/2003 | Jung et al. | 514/242 |
| 2004/0038858 A1 | 2/2004 | Dorsch et al. | |
| 2004/0053942 A1 | 3/2004 | Alberti et al. | 514/256 |
| 2004/0116479 A1 | 6/2004 | Haviv et al. | |
| 2004/0138287 A1 | 7/2004 | Barth et al. | 514/419 |
| 2004/0162281 A1 | 8/2004 | Babu et al. | 514/217.03 |
| 2004/0176446 A1 | 9/2004 | Alonso-Alija et al. | |
| 2004/0242868 A1 | 12/2004 | Angell et al. | 544/59 |
| 2004/0249161 A1 | 12/2004 | Angell et al. | 546/228 |
| 2004/0254200 A1 | 12/2004 | Davis et al. | 514/260.1 |
| 2004/0266839 A1 | 12/2004 | Angell et al. | 514/364 |
| 2004/0267012 A1 | 12/2004 | Angell et al. | 544/60 |
| 2005/0020540 A1 | 1/2005 | Angell et al. | 514/63 |
| 2005/0020590 A1 | 1/2005 | Lang et al. | |
| 2005/0038014 A1 | 2/2005 | Angell et al. | 514/217.12 |
| 2005/0065195 A1 | 3/2005 | Angell et al. | 514/364 |
| 2005/0090491 A1 | 4/2005 | Angell et al. | 514/227.8 |
| 2005/0176964 A1 | 8/2005 | Aston et al. | |
| 2006/0089395 A1 | 4/2006 | Muto et al. | |
| 2006/0122221 A1 | 6/2006 | Angell et al. | |
| 2007/0054942 A1 | 3/2007 | Patel et al. | |
| 2007/0112046 A1 | 5/2007 | Angell et al. | |
| 2007/0142476 A1 | 6/2007 | Angell et al. | |
| 2007/0161673 A1 | 7/2007 | Barker et al. | |
| 2007/0161684 A1 | 7/2007 | Walker et al. | |
| 2009/0023725 A1 | 1/2009 | Bamborough et al. | |
| 2010/0016377 A1 | 1/2010 | Corsi et al. | |

FOREIGN PATENT DOCUMENTS

| | | |
|---|---|---|
| EP | 0 533 268 | 9/1992 |
| EP | 0 346 841 | 6/2003 |
| EP | 0 430 033 | 4/2004 |
| GB | 2 276 161 | 3/1993 |
| GB | 2 276 162 | 3/1993 |
| GB | 2 273 930 | 12/1993 |
| GB | 2 295 387 | 5/1996 |
| JP | 11218884 | 8/1999 |
| WO | WO 94/15920 | 7/1994 |
| WO | WO 95/06636 | 3/1995 |
| WO | WO 95/06644 | 3/1995 |
| WO | WO 95/11243 | 4/1995 |
| WO | WO 95/15954 | 6/1995 |
| WO | WO 95/17401 | 6/1995 |
| WO | 9529907 A1 | 11/1995 |
| WO | WO 95/30675 | 11/1995 |
| WO | WO 96/31508 | 10/1996 |
| WO | WO 96/31509 | 10/1996 |
| WO | WO 97/03034 | 1/1997 |
| WO | WO 98/57934 | 12/1998 |
| WO | WO 99/32463 | 7/1999 |
| WO | WO 00/12074 | 3/2000 |
| WO | WO 00/12497 | 3/2000 |
| WO | WO 00/26216 | 5/2000 |
| WO | WO 00/56738 | 9/2000 |
| WO | 0071510 A2 | 11/2000 |
| WO | WO 00/71493 | 11/2000 |
| WO | WO 00/71509 | 11/2000 |
| WO | WO 00/71511 | 11/2000 |
| WO | WO 01/27089 | 4/2001 |
| WO | WO 01/34605 | 5/2001 |
| WO | 0170695 A1 | 9/2001 |
| WO | WO 01/87875 | 11/2001 |
| WO | 0240486 A2 | 5/2002 |
| WO | WO 02/40486 | 5/2002 |
| WO | 02059083 A2 | 8/2002 |
| WO | WO 03/032970 | 4/2003 |
| WO | 03068747 A1 | 8/2003 |
| WO | WO 03/093248 | 11/2003 |
| WO | WO 2004/010995 | 2/2004 |
| WO | WO 2004/089874 | 10/2004 |
| WO | WO 2004/089875 | 10/2004 |
| WO | WO 2004/089876 | 10/2004 |
| WO | WO 2005/014550 | 2/2005 |
| WO | WO 2005/073189 | 8/2005 |
| WO | WO 2005/073217 | 8/2005 |
| WO | WO 2005/073219 | 8/2005 |
| WO | WO 2005/073232 | 8/2005 |
| WO | 2006104889 A2 | 10/2006 |

OTHER PUBLICATIONS

Boehm, et al., *Expert Opinion of Therapeutic Patents*, vol. 10(1) pp. 25-37 (2000).
Boehm, et al, *Journal of Medicinal Chemistry*, vol. 39(20) pp. 3929-3937 (1996).
Ceccarelli, et al., *European Journal of Medicinal Chemistry*, vol. 33(12) pp. 943-955 (1998).
Courtney, S. et al., *Bioorganic & Medicinal Chemistry Letters*, vol. 14 pp. 3269-3273 (2004).
Foster, et al., *Drug News Perspect.*, vol. 13(8) pp. 488-497 (2000).
Gabriele, et al., *European Journal of Organic Chemistry*, vol. 2001 (24) pp. 4607-4613 (2001).
Han, et al., *Biohemica et Biophysica Acta—Molecular Cell Research*, vol. 1265(2-3) pp. 224-227 (1995).
Hanson, *Expert Opinion on Therapeutic Patents*, vol. 7(7) pp. 729-733 (1997).
Henry, et al., *Drugs of the Future*, vol. 24(12) pp. 1345-1354 (1999).
Henry, J. et al., *Bioogranic & Medicinal Chemistry Letters*, vol. 8 pp. 3335-3340 (1998).
Jiang, et al., *Journal of Biological Chemistry*, vol. 271(30) pp. 17920-17926 (1996).
Li, et al., *Biochemical and Biophysical Research Communications*, vol. 228(2) pp. 334-340 (1996).
Liebeskind, et al., *Organic Letters*, vol. 4 (6) pp. 979-981 (2002).
Marin, et al., *Blood*, vol. 98(3) pp. 667-673 (2001).
Moreland, et al., *Annals of Internal Medicine*, vol. 130(6) pp. 478-486 (1999).
Murali Dhar, et al., *Bioorganic and Medicinal Chemistry Letters*, vol. 12(21) pp. 3125-3128 (2002).
Rankin, et al., *British Journal of Rheumatology*, vol. 34 pp. 334-342 (1995).
Salituro, et al., *Current Medicinal Chemistry*, vol. 6 pp. 807-823 (1999).
Wang, et al., *Journal of Biological Chemistry*, vol. 272(38) pp. 23668-23674 (1997).
U.S. Appl. No. 12/713,448, Aston, N.
Herlaar et al.; "p38 MAPK Signalling Cascades in Inflammatory Disease"; Molecular Medicine Today; 1999; vol. 5; pp. 439-447.
Underwood et al.; "SB239063, a Potent p38 MAP Kinase Inhibitor, Reduces Inflammatory Cytokine Production, Airways Eosinophil Infiltration, and Persistence"; The Journal of Pharmacology and Experimental Therapeutics; 2000; vol. 293, No. 1; pp. 281-288.
Wadsworth et al.; "RWJ 67657, a Potent, Orally Active Inhibitor of p38 Mitogen-Activated Protein Kinase", The Journal of Pharmacology and Experimental Therapeutics; 1999; vol. 291, No. 2; pp. 680-687.

NICOTINAMIDE DERIVATIVES USEFUL AS P38 INHIBITORS

This application is a CON of Ser. No. 11/462,851 filed Aug. 7, 2006, now U.S. Pat. No. 7,709,506, which is CON of Ser. No. 10/503,968 filed Apr. 14, 2005, now U.S. Pat. No. 7,125,898, which is a 371 of PCT/GB03/00554 filed Feb. 10, 2003.

This invention relates to novel compounds and their use as pharmaceuticals, particularly as p38 kinase inhibitors, for the treatment of conditions or disease states mediated by p38 kinase activity or mediated by cytokines produced by the activity of p38 kinase.

We have now found a group of novel compounds that are inhibitors of p38 kinase. According to the invention there is provided a compound of formula (I):

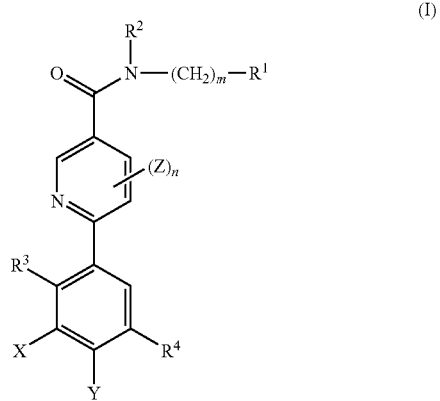

wherein $R_1$ is selected from hydrogen, $C_{1-6}$alkyl optionally substituted by up to three groups selected from $C_{1-6}$alkoxy, halogen and hydroxy, $C_{2-6}$alkenyl, $C_{3-7}$cycloalkyl optionally substituted by one or more $C_{1-6}$alkyl groups, phenyl optionally substituted by up to three groups selected from $R^5$ and $R^6$, and heteroaryl optionally substituted by up to three groups selected from $R^5$ and $R^6$, $R^2$ is selected from hydrogen, $C_{1-6}$alkyl and —$(CH_2)_q$—$C_{3-7}$cycloalkyl optionally substituted by one or more $C_{1-6}$alkyl groups, or $(CH_2)_mR^1$ and $R^2$, together with the nitrogen atom to which they are bound, form a four- to six-membered heterocyclic ring optionally substituted by up to three $C_{1-6}$alkyl groups;

$R^3$ is chloro or methyl; $R^4$ is the group —NH—CO—$R^7$ or —CO—NH—$(CH_2)_q$—$R^8$;

$R^5$ is selected from $C_{1-6}$alkyl, $C_{1-6}$alkoxy, —$(CH_2)_q$—$C_{3-7}$cycloalkyl optionally substituted by one or more $C_{1-6}$alkyl groups, —$CONR^9R^{10}$, —$NHCOR^{10}$, —$SO_2NHR^9$, —$(CH_2)_sNHSO_2R^{10}$, halogen, CN, OH, —$(CH_2)_sNR^{11}R^{12}$, and trifluoromethyl;

$R^6$ is selected from $C_{1-6}$alkyl, $C_{1-6}$alkoxy, halogen, trifluoromethyl and —$(CH_2)_sNR^{11}R^{12}$;

$R^7$ is selected from hydrogen, $C_{1-6}$alkyl, —$(CH_2)_q$—$C_{3-7}$cycloalkyl optionally substituted by one or more $C_{1-6}$alkyl groups, trifluoromethyl, —$(CH_2)_r$heteroaryl optionally substituted by $R^{13}$ and/or $R^{14}$, and —$(CH_2)_r$phenyl optionally substituted by $R^{13}$ and/or $R^{14}$;

$R^8$ is selected from hydrogen, $C_{1-6}$alkyl, $C_{3-7}$cycloalkyl optionally substituted by one or more $C_{1-6}$alkyl groups, $CONHR^9$, phenyl optionally substituted by $R^{13}$ and/or $R^{14}$, and heteroaryl optionally substituted by $R^{13}$ and/or $R^{14}$;

$R^9$ and $R^{10}$ are each independently selected from hydrogen and $C_{1-6}$alkyl, or $R^9$ and $R^{10}$, together with the nitrogen atom to which they are bound, form a five- to six-membered heterocyclic ring optionally containing one additional heteroatom selected from oxygen, sulfur and N-$R^{15}$, wherein the ring may be substituted by up to two $C_{1-6}$alkyl groups;

$R^{11}$ is selected from hydrogen, $C_{1-6}$alkyl and —$(CH_2)_q$—$C_{3-7}$cycloalkyl optionally substituted by one or more $C_{1-6}$alkyl groups, $R^{12}$ is selected from hydrogen and $C_{1-6}$alkyl, or $R^{11}$ and $R^{12}$, together with the nitrogen atom to which they are bound, form a five or six-membered heterocyclic ring optionally containing one additional heteroatom selected from oxygen, sulfur and N-$R^{15}$;

$R^{13}$ is selected from $C_{1-6}$alkyl, $C_{1-6}$alkoxy, —$(CH_2)_q$—$C_{3-7}$cycloalkyl optionally substituted by one or more $C_{1-6}$alkyl groups, —$CONR^9R^{10}$, —$NHCOR^{10}$, halogen, CN, —$(CH_2)_sNR^{11}R^{12}$, trifluoromethyl, phenyl optionally substituted by one or more $R^{14}$ groups and heteroaryl optionally substituted by one or more $R^{14}$ groups;

$R^{14}$ is selected from $C_{1-6}$alkyl, $C_{1-6}$alkoxy, halogen, trifluoromethyl and —$NR^{11}R^{12}$;

$R^{15}$ is selected from hydrogen and methyl;

X and Y are each independently selected from hydrogen, methyl and halogen;

Z is halogen;

m is selected from 0, 1, 2, 3 and 4, wherein each carbon atom of the resulting carbon chain may be optionally substituted with up to two groups selected independently from $C_{1-6}$alkyl and halogen;

n is selected from 0, 1 and 2;

q is selected from 0, 1 and 2;

r is selected from 0 and 1; and s is selected from 0, 1, 2 and 3.

According to a further embodiment of the invention there is provided a compound of formula (IA):

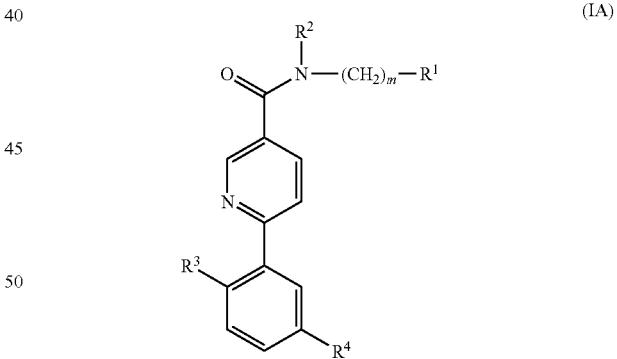

wherein $R^1$, $R^2$, $R^3$, $R^4$ and m are as defined above.

According to one embodiment of the present invention, $R^1$ is selected from hydrogen, $C_{1-6}$alkyl, $C_{3-7}$cycloalkyl, phenyl optionally substituted by $R^5$ and/or $R^6$, and heteroaryl optionally substituted by $R^5$ and/or $R^6$, and $R^2$ is selected from hydrogen, $C_{1-6}$alkyl and —$(CH_2)_q$—$C_{3-7}$cycloalkyl.

In a preferred embodiment, $R^1$ is selected from $C_{1-6}$alkyl, for example methyl, ethyl, n-propyl, isopropyl, 1-methylpropyl, 1,1-dimethylpropyl, 2,2-dimethylpropyl, 1-ethyl-1-methyl-propyl, n-butyl, isobutyl, 3-methylbutyl, 1,1-dimethylbutyl, 1,3-dimethylbutyl, 3,3-dimethylbutyl, 2-pentyl or 1-methylpentyl, optionally substituted by up to three groups selected from $C_{1-6}$alkoxy, in particular $C_{1-4}$alkoxy groups such methoxy or t-butoxy, halogen, in particular fluorine, and hydroxy; $C_{2-6}$alkenyl, for example $C_{4-6}$alkenyl such as 3-methylbut-2-enyl or 1,1-dimethylbut-2-enyl; $C_{3-7}$cycloalkyl optionally substituted by one or more $C_{1-6}$alkyl groups, for example cyclopropyl, cyclobutyl, cyclopentyl or cyclohexyl, in particular cyclopropyl, optionally substituted by one or two $C_{1-4}$alkyl groups such as methyl or ethyl; phenyl optionally substituted by up to three groups selected from $R^5$ and $R^6$, for example phenyl optionally substituted by up to three substituents, for example one or two substituents, such as $C_{1-4}$alkyl, in particular methyl, $C_{1-4}$alkoxy, in particular methoxy, halogen, in particular fluorine or chlorine, trifluoromethyl, —$(CH_2)_sNR^{11}R^{12}$ or —$(CH_2)_sNHSO_2R^{10}$, located on any position on the ring; heteroaryl optionally substituted by up to three groups selected from $R^5$ and $R^6$, for example heteroaryl optionally substituted by one or two substituents, in particular a 5-membered heteroaryl such as furyl, thienyl or thiazolyl optionally substituted by $C_{1-4}$alkyl, in particular methyl. In a particularly preferred embodiment, $R^1$ is $C_{1-6}$alkyl, for example $C_{2-5}$alkyl, such as ethyl, n-propyl, isopropyl, 1-methylpropyl, 1,1-dimethylpropyl, 2,2-dimethylpropyl, n-butyl, isobutyl, 3-methylbutyl or 2-pentyl.

In another preferred embodiment, $R^1$ is selected from $C_{3-7}$cycloalkyl, phenyl optionally substituted by $R^5$ and/or $R^6$, and heteroaryl optionally substituted by $R^5$ and/or $R^6$. In a more preferred embodiment, $R^1$ is selected from $C_{3-6}$cycloalkyl such as cyclopropyl, cyclobutyl, cyclopentyl or cyclohexyl, in particular cyclopropyl, and phenyl optionally substituted by $R^5$ and/or $R^6$. The phenyl may be optionally substituted by one or two substituents, located on any position on the phenyl ring. Preferred substituents for the phenyl include $C_{1-4}$alkoxy, in particular methoxy, —$(CH_2)_sNR^{11}R^{12}$, and —$(CH_2)_sNHSO_2R^{10}$.

In another preferred embodiment, $R^1$ is selected from $C_{1-6}$alkyl, for example n-propyl, 1-methylpropyl, isobutyl, 3-methylbutyl or 2,2-dimethylpropyl, and $C_{3-7}$cycloalkyl optionally substituted by one or more $C_{1-6}$alkyl groups, for example cyclopropyl optionally substituted by one or two methyl groups.

In a further preferred embodiment, $R^1$ is selected from $C_{1-6}$alkyl, for example methyl, ethyl, n-propyl, isopropyl, 1,1-dimethylpropyl, 1-ethyl-1-methyl-propyl, n-butyl, isobutyl, 1,1-dimethylbutyl, 1,3-dimethylbutyl, 3,3-dimethylbutyl, 2-pentyl or 1-methylpentyl, optionally substituted by up to three groups selected from $C_{1-6}$alkoxy, in particular $C_{1-4}$alkoxy groups such methoxy or t-butoxy, halogen, in particular fluorine, and hydroxy; $C_{2-6}$alkenyl, for example $C_{4-6}$alkenyl such as 3-methylbut-2-enyl or 1,1-dimethylbut-2-enyl; $C_{3-7}$cycloalkyl optionally substituted by one or more $C_{1-6}$alkyl groups, for example, cyclopropyl, cyclopentyl or cyclohexyl, optionally substituted by one or two ethyl groups; phenyl optionally substituted by up to three groups selected from $R^5$ and $R^6$, for example phenyl optionally substituted by up to three substituents such as $C_{1-4}$alkyl, in particular methyl, $C_{1-4}$alkoxy, in particular methoxy, halogen, in particular fluorine or chlorine and trifluoromethyl, located on any position on the ring; heteroaryl optionally substituted by up to three groups selected from $R^5$ and $R^6$, in particular a 5-membered heteroaryl such as furyl, thienyl or thiazolyl optionally substituted by $C_{1-4}$alkyl, in particular methyl.

In a preferred embodiment, $R^2$ is selected from hydrogen; $C_{1-4}$alkyl, in particular methyl, ethyl, isopropyl or isobutyl; and —$(CH_2)_q$—$C_{3-6}$cycloalkyl, in particular cyclopropyl, —$CH_2$-cyclopentyl, —$(CH_2)_2$-cyclopentyl or cyclohexyl.

In another preferred embodiment, $R^2$ is selected from hydrogen, $C_{1-4}$alkyl and —$CH_2$-cyclopropyl. More preferably $R^2$ is hydrogen.

In a further preferred embodiment, $(CH_2)_mR^1$ and $R^2$, together with the nitrogen atom to which they are bound, form a four- to six-membered heterocyclic ring optionally substituted by up to three $C_{1-6}$alkyl groups, in particular an azetidinyl, pyrrolidinyl or piperidinyl ring optionally substituted by one or two methyl, ethyl or propyl groups.

In a preferred embodiment, $R^3$ is methyl.

In a preferred embodiment, $R^4$ is the group —CO—NH—$(CH_2)_q$—$R^8$.

In one embodiment of the present invention, $R^5$ is selected from $C_{1-6}$alkyl, $C_{1-6}$alkoxy, —$(CH_2)_q$—$C_{3-7}$cycloalkyl, —$CONR^9R^{10}$, —$NHCOR^{10}$, —$SO_2NHR^9$, —$(CH_2)_s$$NHSO_2R^{10}$, halogen, CN, OH, —$(CH_2)_2NR^{11}R^{12}$, and trifluoromethyl.

In a preferred embodiment, $R^5$ is selected from $C_{1-4}$alkyl, in particular methyl; $C_{1-4}$alkoxy, in particular methoxy; —$(CH_2)_sNHSO_2R^{10}$; halogen, in particular chlorine or fluorine; —$(CH_2)_sNR^{11}R^{12}$; and trifluoromethyl.

In another preferred embodiment, $R^5$ is selected from $C_{1-4}$alkoxy, in particular methoxy, —$(CH_2)_sNR^{11}R^{12}$, and —$(CH_2)_sNHSO_2R^{10}$.

In a further preferred embodiment, $R^5$ is selected from $C_{1-4}$alkyl, in particular methyl; $C_{1-4}$alkoxy, in particular methoxy; halogen, in particular chlorine or fluorine; and trifluoromethyl.

In a preferred embodiment, $R^6$ is selected from $C_{1-4}$alkyl, in particular methyl, ethyl or propyl; $C_{1-4}$alkoxy, in particular methoxy; halogen, in particular chlorine or fluorine; and trifluoromethyl.

In a further preferred embodiment, $R^6$ is $C_{1-4}$alkoxy, in particular methoxy.

In one embodiment of the present invention, $R^7$ is selected from hydrogen, $C_{1-6}$alkyl, —$(CH_2)_q$—$C_{3-7}$cycloalkyl, trifluoromethyl, —$(CH_2)_r$heteroaryl optionally substituted by $R^{13}$ and/or $R^{14}$, and —$(CH_2)_r$phenyl optionally substituted by $R^{13}$ and/or $R^{14}$.

In a preferred embodiment, $R^7$ is selected from $C_{1-6}$alkyl, —$(CH_2)_q$—$C_{3-7}$cycloalkyl, trifluoromethyl, —$(CH_2)_r$heteroaryl optionally substituted by $R^{13}$ and/or $R^{14}$, and —$(CH_2)_r$phenyl optionally substituted by $C_{1-6}$alkyl, $C_{1-6}$alkoxy, —$(CH_2)_q$—$C_{3-7}$cycloalkyl, —$CONR^9R^{10}$, —$NHCOR^{10}$, halogen, CN, trifluoromethyl, phenyl optionally substituted by one or more $R^{14}$ groups and/or heteroaryl optionally substituted by one or more $R^{14}$ groups. In another preferred embodiment, $R^7$ is selected from $C_{1-4}$alkyl, —$(CH_2)_q$—$C_{3-6}$cycloalkyl, trifluoromethyl, —$(CH_2)_r$heteroaryl optionally substituted by $R^{13}$ and/or $R^{14}$, and —$(CH_2)_r$phenyl optionally substituted by $C_{1-6}$alkyl, $C_{1-6}$alkoxy, —$(CH_2)_q$—$C_{3-7}$cycloalkyl, —$CONR^9R^{10}$, —$NHCOR^{10}$, halogen, CN, trifluoromethyl, phenyl optionally substituted by one or more $R^{14}$ groups and/or heteroaryl optionally substituted by one or more $R^{14}$ groups. In a more preferred embodiment, $R^7$ is —$(CH_2)_r$heteroaryl optionally substituted by $R^{13}$ and/or $R^{14}$, in particular a five or six-membered heteroaryl containing at least one heteroatom selected from oxygen, nitrogen and sulfur, for example, pyridinyl optionally substituted by —$NR^{11}R^{12}$, furyl or thiophenyl.

In one embodiment of the present invention, $R^8$ is selected from hydrogen, $C_{1-6}$alkyl, $C_{3-7}$cycloalkyl, $CONHR^9$, phenyl optionally substituted by $R^{13}$ and/or $R^{14}$, and heteroaryl optionally substituted by $R^{13}$ and/or $R^{14}$.

In a preferred embodiment, $R^8$ is selected from $C_{3-7}$cycloalkyl, $CONHR^9$, heteroaryl optionally substituted by $R^{13}$ and/or $R^{14}$, and phenyl optionally substituted by $C_{1-6}$alkyl, $C_{1-6}$alkoxy, —$(CH_2)_q$—$C_{3-7}$cycloalkyl, —$CONR^9R^{10}$, —$NHCOR^{10}$, halogen, CN, trifluoromethyl, phenyl optionally substituted by one or more $R^{14}$ groups and/or heteroaryl optionally substituted by one or more $R^{14}$ groups. In another preferred embodiment, $R^8$ is selected from $C_{3-7}$cycloalkyl, heteroaryl optionally substituted by $R^{13}$ and/or $R^{14}$, and phenyl optionally substituted $C_{1-6}$alkyl, $C_{1-6}$alkoxy, —$(CH_2)_q$—$C_{3-7}$cycloalkyl, —$CONR^9R^{10}$, —$NHCOR^{10}$, halogen, CN, trifluoromethyl, phenyl optionally substituted by one or more $R^{14}$ groups and/or heteroaryl optionally substituted by one or more R$^{14}$ groups. In a more preferred embodiment, R$^8$ is selected from C$_{3-6}$cycloalkyl such as cyclopropyl, cyclobutyl, cyclopentyl or cyclohexyl, in particular cyclopropyl, heteroaryl optionally substituted by R$^{13}$ and/or R$^{14}$, in particular a five or six-membered heteroaryl containing at least one heteroatom selected from nitrogen and sulfur, for example, thiazolyl or thiadiazolyl, and phenyl optionally substituted by heteroaryl. In a particularly preferred embodiment, R$^8$ is selected from C$_{3-6}$cycloalkyl such as cyclopropyl, cyclobutyl, cyclopentyl or cyclohexyl, in particular cyclopropyl.

In a preferred embodiment, R$^9$ is selected from hydrogen and C$_{1-4}$alkyl.

In a preferred embodiment, R$^{10}$ is selected from hydrogen and C$_{1-4}$alkyl, in particular methyl.

In one embodiment, R$^{11}$ is selected from hydrogen, C$_{1-6}$alkyl and —(CH$_2$)$_q$—C$_{3-7}$cycloalkyl optionally substituted by C$_{1-6}$alkyl.

In a preferred embodiment, R$^{11}$ and R$^{12}$, together with the nitrogen atom to which they are bound, form a five or six-membered heterocyclic ring optionally further containing one additional heteroatom N—R$^{15}$.

In one embodiment of the present invention, R$^{13}$ is selected from C$_{1-6}$alkyl, C$_{1-6}$alkoxy, —(CH$_2$)$_q$—C$_{3-7}$cycloalkyl, —CONR$^9$R$^{10}$, —NHCOR$^{10}$, halogen, CN, —(CH$_2$)$_s$NR$^{11}$R$^{12}$, trifluoromethyl, phenyl optionally substituted by one or more R$^{14}$ groups and heteroaryl optionally substituted by one or more R$^{14}$ groups;

In a preferred embodiment, R$^{13}$ is selected from C$_{1-4}$alkyl, in particular methyl, C$_{1-4}$alkoxy, in particular methoxy, halogen, —(CH$_2$)$_s$NR$^{11}$R$^{12}$, phenyl optionally substituted by one or more R$^{14}$ groups and heteroaryl optionally substituted by one or more R$^{14}$ groups. In a more preferred embodiment, R$^{13}$ is selected from —(CH$_2$)$_s$NR$^{11}$R$^{12}$ and heteroaryl optionally substituted by one or more R$^{14}$ groups, in particular a five or six-membered heteroaryl containing at least one nitrogen atom, for example, pyridyl.

In a preferred embodiment R$^{14}$ is selected from from C$_{1-4}$alkyl, in particular methyl, C$_{1-4}$alkoxy, in particular methoxy, and —NR$^{11}$R$^{12}$.

In a preferred embodiment, R$^{15}$ is methyl.

In a preferred embodiment, X and Y are each independently selected from hydrogen, chlorine and fluorine. In a further preferred embodiment, X is fluorine. In another preferred embodiment, Y is hydrogen.

In a preferred embodiment, Z is fluorine.

In one embodiment of the present invention, m is selected from 0, 1, 2, 3 and 4. In another embodiment of the present invention, m is selected from 0, 1, 2, 3 and 4, wherein each carbon atom of the resulting carbon chain may be optionally substituted with up to two groups selected independently from C$_{1-6}$alkyl.

In a preferred embodiment, m is selected from 0, 1, 2 and 3. In a further preferred embodiment, m is selected from 0, 1 and 2, in particular 0 and 1. When the carbon chain of m is substituted, these substituents are preferably one or two methyl groups or fluorine atoms. In one embodiment, the substituents are preferably one or two methyl groups. In another embodiment, the substituents are preferably one or two fluorine atoms.

In a preferred embodiment, n is selected from 0 and 1. In particular, n is 0.

In a preferred embodiment, q is selected from 0 and 1. In particular, q is 0.

In a preferred embodiment, r is 0.

In a preferred embodiment, s is selected from 0 and 1.

It is to be understood that the present invention covers all combinations of particular and preferred groups described hereinabove.

Particular compounds according to the invention include those mentioned in the Examples. Specific examples which may be mentioned include:
6-(5-cyclopropylcarbamoyl-3-fluoro-2-methyl-phenyl)-N-cyclopropylmethyl-nicotinamide;
6-(5-cyclopropylcarbamoyl-3-fluoro-2-methyl-phenyl)-N-(1-cyclopropylethyl)-nicotinamide;
6-(5-cyclopropylcarbamoyl-3-fluoro-2-methyl-phenyl)-N-(2,2-dimethylpropyl)-nicotinamide;
6-(5-cyclopropylcarbamoyl-3-fluoro-2-methyl-phenyl)-N-(2-methylpropyl)-nicotinamide; and
6-(5-cyclopropylcarbamoyl-3-fluoro-2-methyl-phenyl)-N-(1-methylpropyl)-nicotinamide.

Further specific examples which may be mentioned include:
6-(5-cyclopropylcarbamoyl-3-fluoro-2-methyl-phenyl)-N-cyclobutylmethyl-nicotinamide;
6-(5-cyclopropylcarbamoyl-3-fluoro-2-methyl-phenyl)-N-cyclobutyl-nicotinamide;
6-{5-[(cyclopropylamino)carbonyl]-3-fluoro-2-methylphenyl}-N-(2,4,5-trifluorobenzyl)nicotinamide;
6-{5-[(cyclopropylamino)carbonyl]-3-fluoro-2-methylphenyl}-N-(2,5-difluorobenzyl)nicotinamide;
6-{5-[(cyclopropylamino)carbonyl]-3-fluoro-2-methylphenyl}-N-(3,4-difluorobenzyl)nicotinamide;
N-(3-chlorobenzyl)-6-{5-[(cyclopropylamino)carbonyl]-3-fluoro-2-methylphenyl}nicotinamide;
N-(4-chlorobenzyl)-6-{5-[(cyclopropylamino)carbonyl]-3-fluoro-2-methylphenyl}nicotinamide;
N-(3-chloro-2-fluorobenzyl)-6-{5-[(cyclopropylamino)carbonyl]-3-fluoro-2-methylphenyl}nicotinamide;
N-(2-chloro-3,6-difluorobenzyl)-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-(2,3-difluoro-4-methylbenzyl)nicotinamide;
6-{5-[(cyclopropylamino)carbonyl]-3-fluoro-2-methylphenyl}-N-(2,3,5-trifluorobenzyl)nicotinamide;
6-{5-[(cyclopropylamino)carbonyl]-3-fluoro-2-methylphenyl}-N-(3-fluoro-4-methylbenzyl)nicotinamide;
N-(5-chloro-2-fluorobenzyl)-6-{5-[(cyclopropylamino)carbonyl]-3-fluoro-2-methylphenyl}nicotinamide;
N-(2-chlorobenzyl)-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-(4-fluorobenzyl)nicotinamide;
6-{5-[(cyclopropylamino)carbonyl]-3-fluoro-2-methylphenyl}-N-(2,3,4-trifluorobenzyl)nicotinamide;
N-benzyl-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-[3-(trifluoromethyl)benzyl]nicotinamide;
6-{5-[(cyclopropylamino)carbonyl]-3-fluoro-2-methylphenyl}-N-(1,1-dimethylbutyl)nicotinamide;
N-(4-chloro-2-fluorobenzyl)-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-[4-(trifluoromethyl)benzyl]nicotinamide;
6-{5-[(cyclopropylamino)carbonyl]-3-fluoro-2-methylphenyl}-N-[(5-methyl-2-furyl)methyl]nicotinamide;
6-{5-[(cyclopropylamino)carbonyl]-3-fluoro-2-methylphenyl}-N-(2,3-difluorobenzyl)nicotinamide;
N-(3-chloro-4-fluorobenzyl)-6-{5-[(cyclopropylamino)carbonyl]-3-fluoro-2-methylphenyl}nicotinamide;
6-{5-[(cyclopropylamino)carbonyl]-3-fluoro-2-methylphenyl}-N-(4-methylbenzyl)nicotinamide;
6-{5-[(cyclopropylamino)carbonyl]-3-fluoro-2-methylphenyl}-N-[(3-methylthien-2-yl)methyl]nicotinamide;
N-(3-chloro-2,6-difluorobenzyl)-6-{5-[(cyclopropylamino)carbonyl]-3-fluoro-2-methylphenyl}nicotinamide;

6-{5-[(cyclopropylamino)carbonyl]-3-fluoro-2-methylphenyl}-N-(1-ethyl-1-methylpropyl)nicotinamide;
6-{5-[(cyclopropylamino)carbonyl]-3-fluoro-2-methylphenyl}-N-(2-fluorobenzyl)nicotinamide;
6-{5-[(cyclopropylamino)carbonyl]-3-fluoro-2-methylphenyl}-N-(tert-pentyl)nicotinamide; and
6-{5-[(cyclopropylamino)carbonyl]-3-fluoro-2-methylphenyl}-N-(3-methylbenzyl)nicotinamide.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl and t-butyl. A $C_{1-4}$alkyl group is preferred, for example methyl, ethyl, isopropyl or t-butyl. The said alkyl groups may be optionally substituted with one or more fluorine atoms for example, trifluoromethyl.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2, and at most 6, carbon atoms and containing at least one double bond. Examples of "alkenyl" as used herein include, but are not limited to ethenyl, propenyl, 3-methylbut-2-enyl and 1,1-dimethylbut-2-enyl.

As used herein, the term "alkoxy" refers to a straight or branched chain alkoxy group, for example, methoxy, ethoxy, propoxy, prop-2-oxy, butoxy, but-2-oxy, 2-methylprop-1-oxy, 2-methylprop-2-oxy, pentoxy, or hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms which may optionally contain up to one double bond. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-6}$cycloalkyl group is preferred, for example, cyclopropyl, cyclopentyl or cyclohexyl. The said cycloalkyl groups may be optionally substituted with one or more $C_{1-6}$alkyl groups, for example one or two methyl groups. In one embodiment, the cycloalkyl groups may be optionally substituted by up to four $C_{1-6}$alkyl groups, for example one or two $C_{1-6}$alkyl groups, in particular one or two $C_{1-4}$alkyl groups such as methyl or ethyl.

As used herein, the terms "heteroaryl ring" and "heteroaryl" refer to a monocyclic five- to seven-membered unsaturated hydrocarbon ring containing at least one heteroatom independently selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The said ring may be optionally substituted by one or more substituents independently selected from $C_{1-6}$alkyl and oxy.

As used herein, the terms "heterocyclic ring" or "heterocyclyl" refer to a monocyclic three- to seven-membered saturated hydrocarbon ring containing at least one heteroatom independently selected from oxygen, nitrogen and sulfur. Preferably, the heterocyclyl ring has five or six ring atoms. Examples of heterocyclyl groups include, but are not limited to, pyrrolidinyl, imidazolidinyl, pyrazolidinyl, piperidyl, piperazinyl, morpholino, tetrahydropyranyl, tetrahydrofuranyl, and thiomorpholino. The said ring may be optionally substituted by one or more substituents independently selected from $C_{1-6}$alkyl and oxy.

As used herein, the terms "halogen" or "halo" refer to the elements fluorine, chlorine, bromine and iodine. Preferred halogens are fluorine, chlorine and bromine. A particularly preferred halogen is fluorine or chlorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. All such solvates are included within the scope of the present invention.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

Salts of the compounds of the present invention are also encompassed within the scope of the invention and may, for example, comprise acid addition salts resulting from reaction of an acid with a basic nitrogen atom present in a compound of formula (I).

Salts encompassed within the term "pharmaceutically acceptable salts" refer to non-toxic salts of the compounds of this invention. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. Other salts which are not pharmaceutically acceptable may be useful in the preparation of compounds of this invention and these form a further aspect of the invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working examples.

A compound of formula (I) may be prepared by reacting a compound of (II)

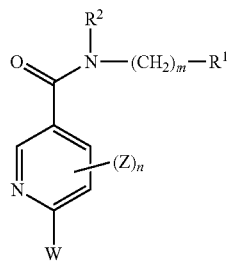

(II)

in which $R^1$, $R^2$, Z, m and n are as hereinbefore defined and W is halogen, in particular bromine or chlorine,
with a compound of formula (III)

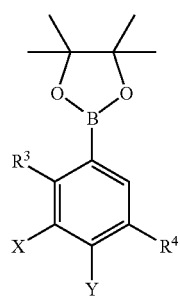

(III)

in which $R^3$, $R^4$, X and Y are as hereinbefore defined,
in the presence of a catalyst, for example tetrakis(triphenylphosphine)palladium.

A compound of formula (II) may readily be prepared from a corresponding acid compound of formula (IV)

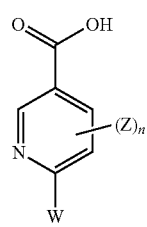

(IV)

in which Z, W and n are as hereinbefore defined,
by converting the acid to an activated form of the acid, for example the acid chloride, by treatment with, for example, thionyl chloride, and then reacting the activated acid thus formed with an amine compound of formula (V)

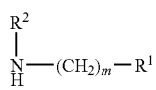

(V)

in which $R^1$, $R^2$ and m are as hereinbefore defined,
under amide forming conditions.

Suitable amide forming conditions are well known in the art and include treating a solution of the acid of formula (IV), or the activated form thereof, in for example acetone or dichloromethane, with an amine of formula (V) in the presence of sodium carbonate.

A compound of formula (III) may be prepared by reacting a compound of formula (VI)

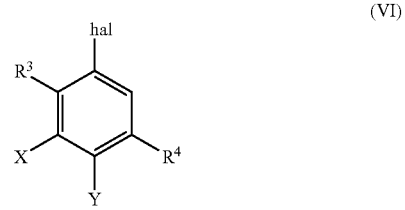

(VI)

in which $R^3$, $R^4$, X and Y are as hereinbefore defined and hal is halogen, in particular iodine,
with bis(pinnacolato)diboron, $PdCl_2dppf$ and potassium acetate in a solvent such as DMF.

Alternatively, when $R^4$ is $-CO-NH-(CH_2)_q-R^8$, a compound of formula (III) may be prepared by reacting an acid compound of formula (VII)

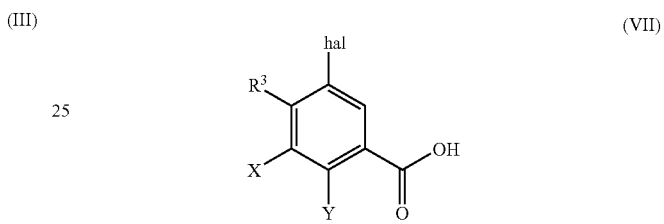

(VII)

in which $R^3$, hal, X and Y are as hereinbefore defined,
with bis(pinnacolato)diboron, $PdCl_2dppf$ and potassium acetate in a solvent such as DMF, and then forming an amide by reaction with an amine compound of formula (V) as hereinbefore defined.

A compound of formula (I) may also be prepared by reacting a compound of formula (VIII)

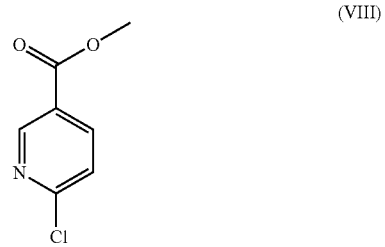

(VIII)

with a compound of formula (III) as hereinbefore defined and then reacting the acid thus formed with an amine of formula (V) as hereinbefore defined, under amide forming conditions.

Additionally, a compound of formula (I) may be prepared by reacting a compound of (II) as hereinbefore defined with a compound of formula (IX)

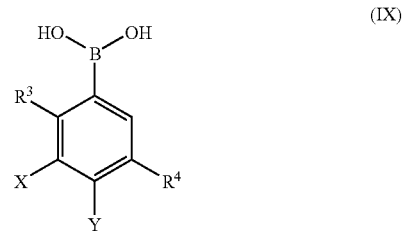

(IX)

in which $R^3$, $R^4$, X and Y are as hereinbefore defined,
in the presence of a catalyst, for example tetrakis(triphenylphosphine)palladium.

For example, one general method for preparing the compounds of formula (I) comprises the reactions set out in Scheme 1 below.

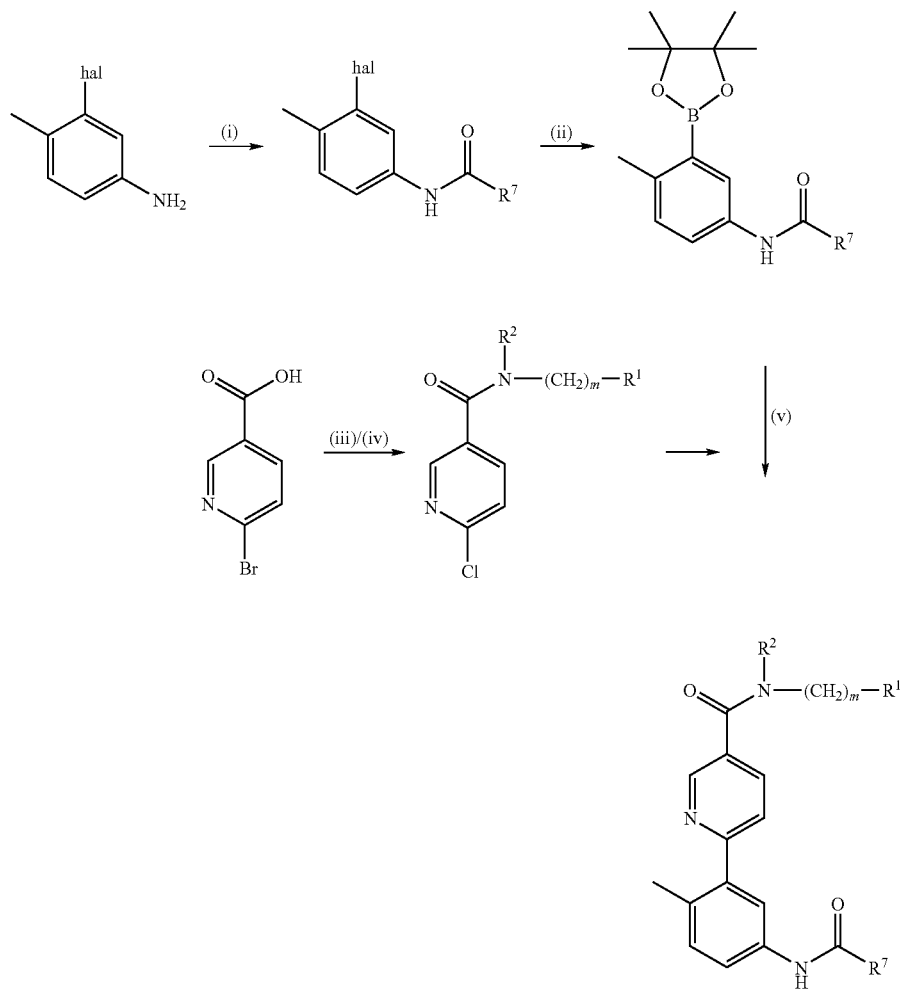

i. $R^7CO_2H$, HATU, DIPEA, DMF.
ii. Bis(pinnacolato)diboron, $PdCl_2dppf$, KOAc, DMF.
iii. $SOCl_2$.
iv. $R^1(CH_2)_mR^2NH$, $Na_2CO_3$, acetone.
v. $Na_2CO_3$, tetrakis(triphenylphosphine)palladium, propan-2-ol.

For example, another general method for preparing the compounds of formula (I) comprises the reactions set out in Scheme 2 below.

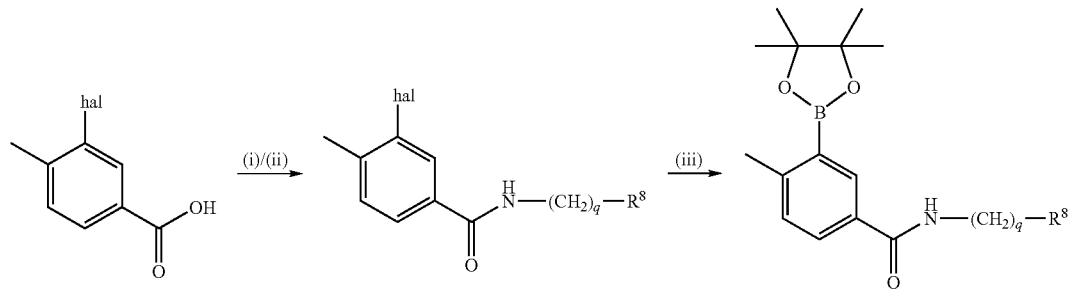

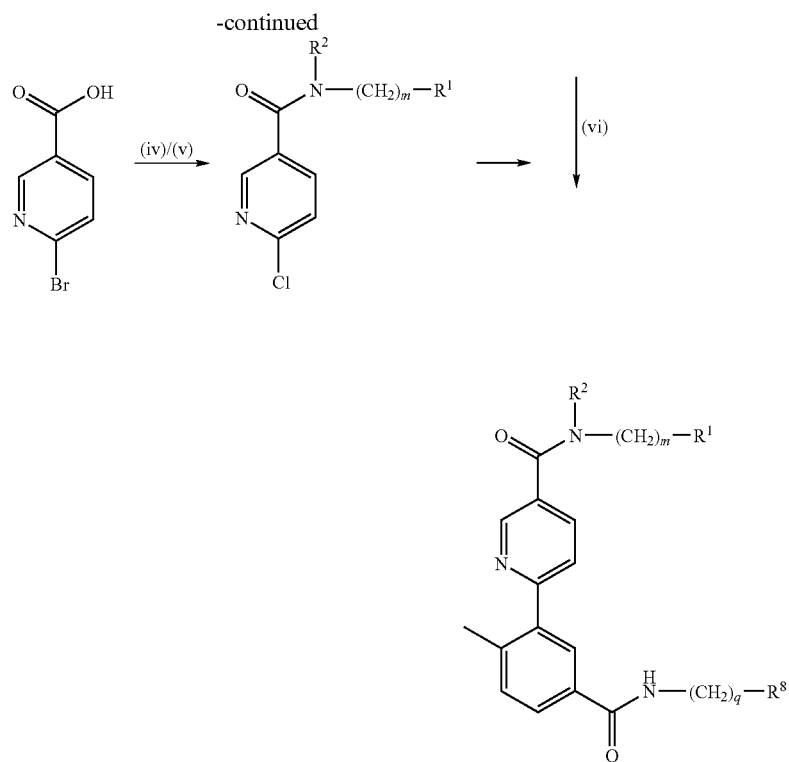
i. SOCl$_2$.
ii. R$^8$(CH$_2$)$_q$NH$_2$, Na$_2$CO$_3$, acetone.
iii. Bis(pinnacolato)diboron, PdCl$_2$dppf, KOAc, DMF.
iv. SOCl$_2$.
v. R$^1$(CH$_2$)$_m$R$^2$NH, Na$_2$CO$_3$, acetone.
vi. Na$_2$CO$_3$, tetrakis(triphenylphosphine)palladium, propan-2-ol.
For example, another general method for preparing the compounds of formula (I) comprises the reactions set out in Scheme 3 below.
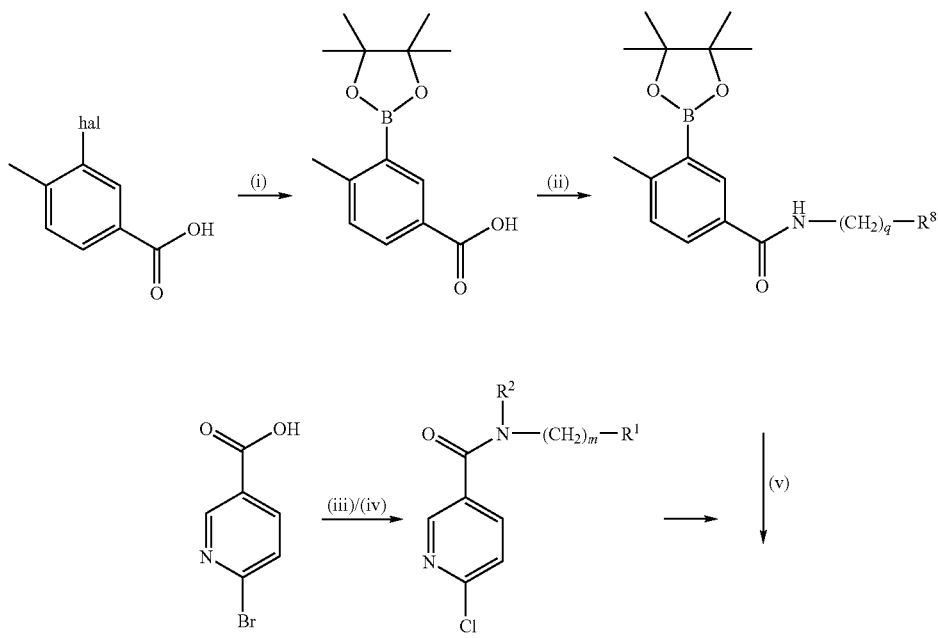

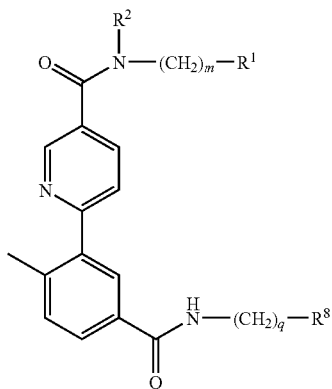

i. Bis(pinnacolato)diboron, PdCl₂dppf, KOAc, DMF.
ii. R⁸(CH₂)qNH₂, HATU, DIPEA, DMF.
iii. SOCl₂.
iv. R¹(CH₂)mR²NH, Na₂CO₃, DCM.
v. Na₂CO₃, tetrakis(triphenylphosphine)palladium, propan-2-ol.

For example, another general method for preparing the compounds of formula (I) comprises the reactions set out in Scheme 4 below.

Scheme 4

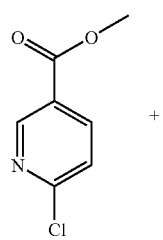

+

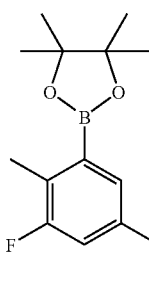

(i)

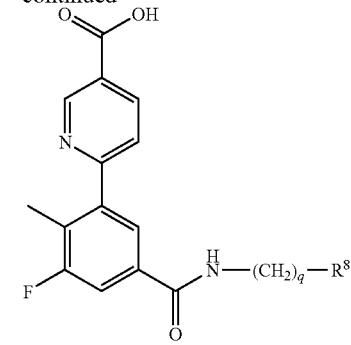

(ii)

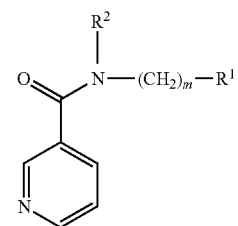

i. NaHCO₃, tetrakis(triphenylphosphine)palladium, propan-2-ol.
ii. R¹(CH₂)mR²NH, HATU, DIPEA, DMF.

For example, a further general method for preparing the compounds of formula (I) comprises the reactions set out in Scheme 5 below.

Scheme 5

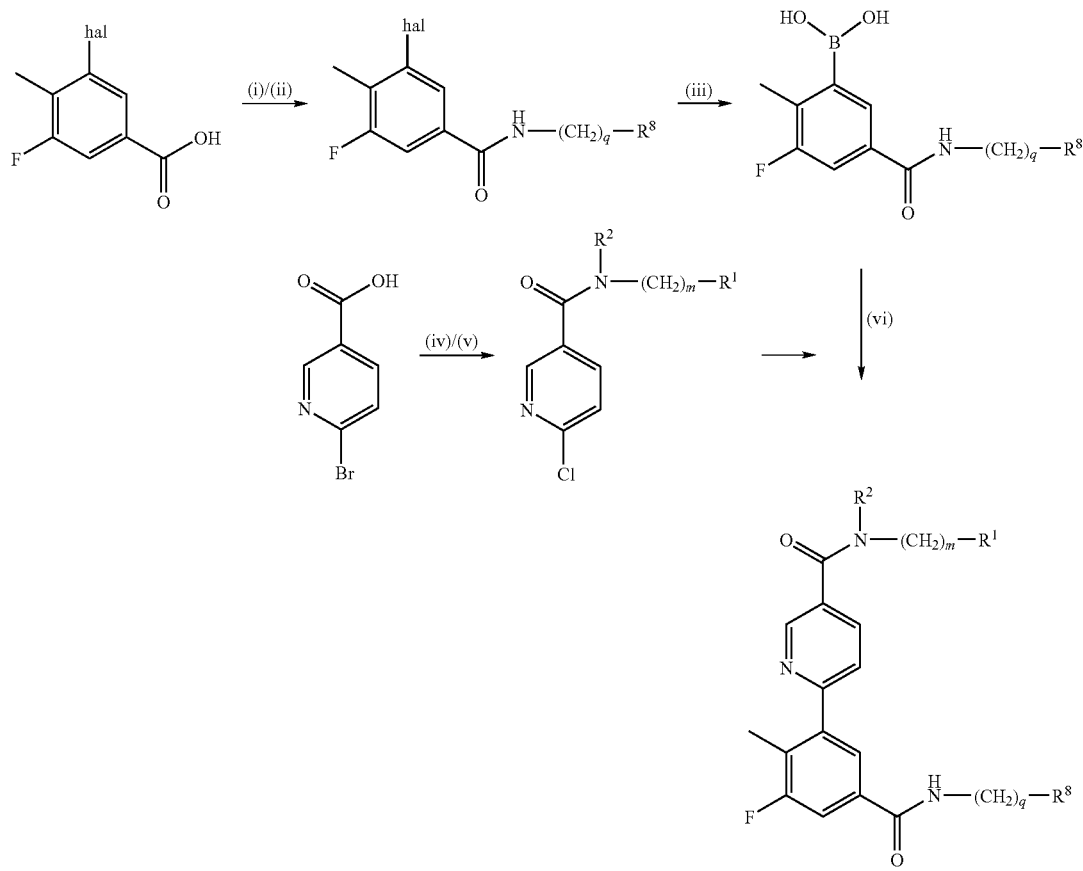

i. SOCl$_2$.
ii. R$^8$(CH$_2$)$_q$NH$_2$, Na$_2$CO$_3$, DCM.
iii. NaH, n-BuLi, THF, (iPrO)$_3$B.
iv. SOCl$_2$.
v. R$^1$(CH$_2$)$_m$R$^2$NH, Na$_2$CO$_3$, DCM.
vi. NaHCO$_3$, tetrakis(triphenylphosphine)palladium, propan-2-ol.

Whilst it is possible for the compounds of the present invention to be administered as the new chemical, the compounds of formula (I) are conveniently administered in the form of pharmaceutical compositions. Thus, in another aspect of the invention, we provide a pharmaceutical composition comprising a compound of formula (I), in admixture with one or more pharmaceutically acceptable carriers, diluents or excipients.

The compounds of formula (I) may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I). A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 µg/kg body weight. In most cases they will be administered in one or more doses in an amount not in excess of about 20 mg/kg body weight per day. Preferably, in most cases, dose is from about 100 µg/kg to about 5 mg/kg body weight, daily. For administration particularly to mammals, and particularly humans, it is expected that the daily dosage level of the active agent will be from 0. 1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

In another aspect, the present invention provides a compound of formula (I) for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

It will be appreciated that the compounds of the invention may be selective for one or more of the isoforms of p38, for example p38α, p38β, p38γ and/or p38δ. In one embodiment, the compounds of the invention selectively inhibit the p38α isoform. In another embodiment, the compounds of the invention selectively inhibit the p38β isoform. In a further embodiment, the compounds of the invention selectively inhibit the p38α and p38β isoforms. Assays for determining the selectivity of compounds for the p38 isoforms are described in, for example, WO 99/61426, WO 00/71535 and WO 02/46158.

It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a method for the treatment of a condition or disease state mediated by p38 kinase activity, or mediated by cytokines produced by the activity of p38 kinase, in a subject which comprises administering to said subject a therapeutically effective amount of a compound of formula (I). The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 kinase activity in a subject, e.g. a human, which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments.

The compounds of the present invention can be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula (I).

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I).

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I).

A further aspect of the invention provides a method of treatment of a human or animal subject suffering from rheumatoid arthritis, asthma, chronic pulmonary inflammation, chronic obstructive pulmonary disease, neurodegenerative disease, Alzheimer's disease, Parkinson's disease and epilepsy which comprises administering to said subject a therapeutically effective amount of a compound of formula (I).

A further aspect of the invention provides a method of treatment of a human or animal subject suffering from any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable salt or solvate thereof.

The compounds of formula (I) may be employed alone or in combination with other therapeutic agents for the treatment of the above-mentioned conditions. In particular, in rheumatoid arthritis therapy, combination with other chemotherapeutic or antibody agents is envisaged. Combination therapies according to the present invention thus comprise the administration of at least one compound of formula (I) and at least one other pharmaceutically active agent. The compound(s) of formula (I) and the other pharmaceutically active agent(s) may be administered together or separately and, when administered separately, this may occur separately or sequentially in any order. The amounts of the compound(s) of formula (I) and the other pharmaceutically active agent(s) and the relative timings of administration will be selected in order to achieve the desired combined therapeutic effect. Examples of other pharmaceutically active agents which may be employed in combination with compounds of formula (I) for rheumatoid arthritis therapy include: immunosuppresants such as amtolmetin guacil, mizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

EXAMPLES

The following examples are illustrative embodiments of the invention, not limiting the scope of the invention in any way. Reagents are commercially available or are prepared according to procedures in the literature.

LCMS was conducted on a column (3.3cm×4.6 mm ID, 3 um ABZ+PLUS), at a Flow Rate of 3 ml/min, Injection Volume of 5 μl, at room temperature and UV Detection Range at 215 to 330 nm.

Intermediate 1

6-Chloro-N-cyclopropylmethylnicotinamide

6-Bromonicotinic acid (200 mg, 0.99 mmol) was heated at reflux in thionyl chloride (2 ml) for 2.5 hrs. The reaction was allowed to cool to room temperature and the excess thionyl chloride evaporated under vacuum. The residue was dissolved in acetone (4 ml), cyclopropylmethylamine (71 mg, 0.10 mmol) and sodium carbonate (500 mg) were added to the solution. The reaction was stirred at room temperature for 4 hrs, filtered and the filtrate reduced to dryness under vacuum to give 6-chloro-N-cyclopropylmethylnicotinamide as a cream solid. NMR: δH [$^2$H$_6$]-DMSO 8.82,(2H, m), 8.23,(1H, dd), 7.63,(1H, d), 3.14,(2H, t), 1.01,(1H, m), 0.44,(2H, m), 0.22,(2H, m).

Intermediate 2

6-Chloro-N-(4-methoxyphenyl)nicotinamide

6-Bromonicotinic acid (200 mg, 0.99 mmol) was heated at reflux in thionyl chloride (2 ml) for 3 hrs. The reaction was allowed to cool to room temperature and the excess thionyl chloride evaporated under vacuum. The residue was dissolved in DCM (2 ml), p-anisidine (123 mg, 0.10 mmol) and sodium carbonate (500 mg) were added to the solution. The reaction was stirred at room temperature for 4 hrs, filtered and the filtrate reduced to dryness under vacuum to give 6-chloro-N-(4-methoxyphenyl)nicotinamide. NMR: δH [$^2$H$_6$]-DMSO 10.37,(1H, b), 8.94,(1H, d), 8.34,(1H, dd), 7.70,(1H, d), 7.66, (2H, m), 6.95,(2H, m), 3.75,(3H, s).

Intermediate 3

6-Chloro-N-(3-methoxybenzyl)nicotinamide

6-Bromonicotinic acid (200 mg, 0.99 mmol) was heated at reflux in thionyl chloride (2 ml) for 3 hrs. The reaction was allowed to cool to room temperature and the excess thionyl chloride evaporated under vacuum. The residue was dissolved in DCM (2 ml), 3-methoxybenzylamine (137 mg, 0.10 mmol) and sodium carbonate (500 mg) were added to the solution. The reaction was stirred at room temperature for 4 hrs, filtered and the filtrate reduced to dryness under vacuum to give 6-chloro-N-(3-methoxybenzyl)nicotinamide. NMR: δH [$^2$H$_6$]-DMSO 9.29,(1H, t), 8.88,(1H, d), 8.28,(1H, dd), 7.66,(1H, d), 7.25,(1H, t), 6.90,(2H, m), 6.83,(1H, m), 4.47, (2H, d), 3.74,(3H, s).

Intermediate 4

6-Chloro-N-(3-methylsulphonylaminobenzthnicotinamide

6-Bromonicotinic acid (200 mg, 0.99 mmol) was heated at reflux in thionyl chloride (2 ml) for 3 hrs. The reaction was allowed to cool to room temperature and the excess thionyl chloride evaporated under vacuum. The residue was dissolved in DCM (2 ml), 3-methylsulphonylaminobenzylamine (200 mg, 0.10 mmol) and sodium carbonate (500 mg) were added to the solution. The reaction was stirred at room temperature for 4 hrs, filtered and the filtrate reduced to dryness under vacuum to give 6-chloro-N-(3-methylsulphonylaminobenzyl)nicotinamide. NMR: δH [$^2$H$_6$]-DMSO 9.30, (1H, t), 8.88,(1H, d), 8.28,(1H, dd), 7.67,(1H, d), 7.23,(1H, t), 7.10,(1H, s), 7.04,91H, d), 6.97,(1H, d), 4.45,(2H, d), 2.90, (3H, s).

Intermediate 5

6-Chloro-N-[2-(4-methylpiperazin-1-yl)phenyl]nicotinamide

6-Bromonicotinic acid (200 mg, 0.99 mmol) was heated at reflux in thionyl chloride (2 ml) for 3 hrs. The reaction was allowed to cool to room temperature and the excess thionyl chloride evaporated under vacuum. The residue was dissolved in DCM (2 ml), 1-(2-aminobenzyl)-4-methylpiperazine (205 mg, 0.10 mmol) and sodium carbonate (500 mg) were added to the solution. The reaction was stirred at room temperature for 4 hrs, filtered and the filtrate reduced to dryness under vacuum to give 6-chloro-N-[2-(4-methylpiperazin-1-yl)phenyl]nicotinamide. NMR: δH [$^2$H$_6$]-DMSO 11.62,(1H, s), 8.95,(1H, d), 8.32,(1H, dd), 8.25,(1H, d), 7.77, (1H, d), 7.34,(1H, m), 7.28,(1H, m), 7.10,(1H, m), 3.73,(2H, s), 2.56-2.20,(8H, b), 2.12,(3H, s).

Intermediate 6

4-Methyl-N-(3-pyridin-2-yl-phenyl)-3-(4,4,5,5-tetramethyl-[1,3,2]dioxaborolan-2-yl)-benzamide 3-Iodo-4-methyl-N-(3-pyridin-2-yl-phenyl)benzamide (Intermediate 7) (83 mg, 0.20 mmol), bis(pinnacolato)diboron (100 mg, 0.39 mmol), potassium acetate (97 mg, 1.0 mmol) and PdCl$_2$dppf (12 mg) were heated at 80° C. in DMF (2.5 ml) for 4 hrs. The cooled reaction was absorbed onto silica, applied to a bond-elut (10 g, silica) and eluted with an ethylacetate/cyclohexane gradient (0 to 100%). The solvent was evaporated from the product fractions under vacuum and the residue triturated with ether to give 4-methyl-N-(3-pyridin-2-yl-phenyl)-3-(4,4,5,5-tetramethyl-[1,3,2]dioxaborolan-2-yl)-benzamide as a white solid (31 mg). LCMS: retention time 3.69 min, MH$^+$ 415.

Intermediate 7

3-Iodo-4-methyl-N-(3-pyridin-2-yl-phenyl)benzamide

3-Iodo-4-methylbenzoic acid (154 mg, 0.59 mmol) was heated at 80° C. in thionyl chloride (2 ml) for 3 hrs. The reaction was allowed to cool to room temperature and the excess thionyl chloride evaporated under vacuum. The residue was dissolved in acetone (3 ml), 2-(3-aminophenyl)pyridine (100 mg, 0.59 mmol) and sodium carbonate (400 mg) were added to the solution. The reaction was stirred at room temperature for 11 days, filtered and the filtrate reduced to dryness under vacuum. The residue was dissolved in ether and filtered through a bond-elut (1 g, silica), washing with ether. The solvent was evaporated from the combined filtrate and washings to give 3-iodo-4-methyl-N-(3-pyridin-2-yl-phenyl)benzamide as a cream foam. NMR: δH CDCl$_3$ 8.70, (1H, dt), 8.33,(1H, d), 8.18,(1H, t), 7.93-7.89,(2H, m), 7.79-7.75,(4H, m), 7.50,(1H, t), 7.35,(1H, d), 7.26,(1H, m), 2.51, (3H, s).

Intermediate 8

N-Cyclopropyl-4-methyl-3-(4,4,5,5-tetramethyl-[1,3,2]dioxaborolan-2-yl)-benzamide N-Cyclopropyl-3-iodo-4-methylbenzamide (Intermediate 9) (1.1 g, 3.64 mmol), bis(pinnacolato)diboron (1.85 g, 7.28 mmol), potassium acetate (1.79 g, 18.2 mmol) and PdCl$_2$dppf (55 mg) were heated at 85° C. in DMF (30 ml) for 4.5 hrs. The cooled reaction was absorbed onto silica, applied to a bond-elut (10 g, silica) and eluted with an ethylacetate/cyclohexane gradient (0 to 100%). The solvent was evaporated from the product fractions under vacuum and the residue triturated with cyclohexane to give N-cyclopropyl-4-methyl-3-(4,4,5,5-tetramethyl-[1,3,2]dioxaborolan-2-yl)-benzamide as a white solid (650 mg). NMR: δH [$^2$H$_6$]-DMSO 8.40,(1H, d), 8.06,(1H, d), 7.76,(1H, dd), 7.23,(1H, d), 2.82,(1H, m), 2.48, (3H, s), 1.30,(12H, s), 0.66,(2H, m), 0.56,(2H, m).

Intermediate 9

N-Cyclopropyl-3-iodo-4-methylbenzamide

3-Iodo-4-methylbenzoic acid (1.0 g, 3.8 mmol) was heated at 80° C. in thionyl chloride (10 ml) for 2 hrs. The reaction was allowed to cool to room temperature and the excess thionyl chloride evaporated under vacuum. The residue was dissolved in DCM (10 ml), cyclopropylamine (0.32 ml) and sodium carbonate (2.0 g) were added to the solution. The reaction was stirred at room temperature for 18 hrs, filtered and the filtrate reduced to dryness under vacuum. The residue was triturated with ether to give N-cyclopropyl-3-iodo-4-methylbenzamide as a white solid (1.1 g). NMR: δH [$^2$H$_6$]-DMSO 8.46,(1H, d), 8.24,(1H, d), 7.74,(1H, dd), 7.38,(1H, d), 2.82,(1H, m), 2.38,(3H, s), 0.67,(2H, m), 0.55,(2H, m).

Intermediate 10

N-Cyclopropylmethyl-4-methyl-3-(4,4,5,5-tetramethyl-[1,3,2]dioxaborolan-2-yl)-benzamide 4-Methyl-3-(4,4,5,5-tetramethyl-[1,3,2]dioxaborolan-2-yl)-benzoic acid (Intermediate 17) (2.0 g, 7.63 mmol), DIPEA (4 ml, 22.89 mmol) and HATU (3.05 g, 8.02 mmol) were dissolved in DMF (20 ml) and stirred at room temperature for 15 mins. Cyclopropylmethylamine (568 mg, 8.01 mmol) was added and the reaction stirred at room temperature for 18 hours. The solvent was evaporated under vacuum and the reaction partitioned between ethyl acetate (250 ml) and water (50 ml). The organic phase was washed with hydrochloric acid (2N, 50 ml) and aqueous sodium bicarbonate (1M, 50 ml), then dried (magnesium sulphate) and the solvent evaporated under vacuum. The residue was absorbed onto silica and purified by flash column chromatography eluting with cyclohexane/ethyl acetate (4:1). The solvent was evaporated from the product fractions under vacuum to give N-cyclopropylmethyl-4-methyl-3-(4,4,5,5-tetramethyl-[1,3,2]dioxaborolan-2-yl)-benzamide (1.73 g). LCMS: retention time 3.47 min, MH$^-$ 316. NMR: δH [$^2$H$_6$]-DMSO 8.54,(1H, t), 8.11,(1H, d), 7.82,(1H, dd), 7.26,(1H, d), 3.12,(2H, t), 1.32, (12H, s), 1.03,(1H, m), 0.42,(2H, m), 0.22,(2H, m).

Intermediate 11

4-Methyl-3-(4,4,5,5-tetramethyl-[1,3,2]dioxaborolan-2-yl)-N-(thiazol-2-yl)-benzamide 4-Methyl-3-(4,4,5,5-tetramethyl-[1,3,2]dioxaborolan-2-yl)-benzoic acid (2.0 g, 7.63 mmol), DIPEA (4 ml, 22.89 mmol) and HATU (3.05 g, 8.02 mmol) were dissolved in DMF (20 ml) and stirred at room temperature for 15 mins. 2-Aminothiazole (801 mg, 8.01 mmol) was added and the reaction stirred at room temperature for 18 hours. The solvent was evaporated under vacuum and the reaction partitioned between ethyl acetate (250 ml) and water (50 ml). The organic phase was washed with hydrochloric acid (2N, 50 ml) and aqueous sodium bicarbonate (1M, 50 ml), then dried (magnesium sulphate) and the solvent evaporated under vacuum. The residue was absorbed onto silica and purified by flash column chromatography eluting with cyclohexane/ethyl acetate (4:1). The solvent was evaporated from the product fractions under vacuum to 4-methyl-3-(4,4,5,5-tetramethyl-[1,3,2]dioxaborolan-2-yl)-N-(thiazol-2-yl)-benzamide (1.72 g). LCMS: retention time 3.66 min, MH$^-$ 345. NMR: δH [$^2$H$_6$]-DMSO 12.65,(1H, b), 8.32,(1H, d), 8.08,(1H, dd), 7.56,(1H, d), 7.35,(1h, d), 7.28,(1H, d), 2.54,(3H, s), 1.34, (12H, s).

Intermediate 12

4-Methyl-3-(4,4,5,5-tetramethyl-[1,3,2]dioxaborolan-2-yl)-N-(thiadiazol-2-yl)-benzamide 4-Methyl-3-(4,4,5,5-tetramethyl-[1,3,2]dioxaborolan-2-yl)-benzoic acid (2.0 g, 7.63 mmol), DIPEA (4 ml, 22.89 mmol) and HATU (3.05 g, 8.02 mmol) were dissolved in DMF (20 ml) and stirred at room temperature for 15 mins. 2-Aminothiadiazole (810 mg, 8.01 mmol) was added and the reaction stirred at room temperature for 18 hours. The solvent was evaporated under vacuum and the reaction partitioned between ethyl acetate (250 ml) and hydrochloric acid (2N, 150 ml). The aqueous was extracted with ethylacetate (2×250 ml). The combined organic extracts were dried (magnesium sulphate) and the solvent evaporated under vacuum. The residue was absorbed onto silica and purified by flash column chromatography eluting with cyclohexane/ethyl acetate (4:1 then 1:1). The solvent was evaporated from the product fractions under vacuum to 4-methyl-3-(4,4,5,5-tetramethyl-[1,3,2]dioxaborolan-2-yl)-N-(thiadiazol-2-yl)-benzamide (0.95 g). LCMS: retention time 3.34 min, MH⁻ 346. NMR: δH [²H₆]-DMSO 13.08,(1H, b), 9.22,(1H, s), 8.35,(1H, d), 8.11, (1H, dd), 7.38,(1H, d), 2.55,(3H, s), 1.34,(12H, s).

Intermediate 13

N-[4-Methyl-3-(4,4,5,5-tetramethyl-[1,3,2]dioxaborolan-2-yl)-phenyl]-3-furamide

N-(3-Iodo-4-methylphenyl)-3-furamide (Intermediate 15) (2.5 g, 7.64 mmol), bis(pinnacolato)diboron (2.13 g, 8.41 mmol), potassium acetate (825 mg, 8.41 mmol) and PdCl₂dppf (312 mg, 0.38 mmol) in DMF (20 ml) were heated at 80° C. for 20 hrs. The cooled reaction was absorbed onto silica and applied to a bond-elut (silica, 10 g) and eluted with a cyclohexane/ethyl acetate gradient. The product fractions were concentrated under vacuum, dissolved in DMF (40 ml) and reacted with bis(pinnacolato)diboron (7.76 g, 30.57 mmol), potassium acetate (3.0 g, 30.57 mmol) and PdCl₂dppf (249 mg, 0.306 mmol) at 80° C. for 23 hrs. The cooled reaction was absorbed onto silica and applied to bond-eluts (silica, 2×10 g) and eluted with a cyclohexane/ethyl acetate gradient. The product fractions were concentrated under vacuum to give N-[4-methyl-3-(4,4,5,5-tetramethyl-[1,3,2] dioxaborolan-2-yl)-phenyl]-3-furamide. LCMS: retention time 3.55 min, MH⁺ 328. NMR: δH [²H₆]-DMSO 9.86,(1H, b), 8.36,(1H, m), 7.86-7.82,(2H, m), 7.77,(1H, t), 7.14,(1H, d), 6.99,(1H, m), 2.41,(3H, s), 1.30,(12H, s).

Intermediate 14

N-[4-Methyl-3-(4,4,5,5-tetramethyl-[1,3,2]dioxaborolan-2-yl)-phenyl]thiophene-3-amide N-(3-Iodo-4-methylphenyl)thiophene-3-amide (Intermediate 16) (2.64 g, 7.64 mmol), bis(pinnacolato)diboron (2.13 g, 8.41 mmol), potassium acetate (825 mg, 8.41 mmol) and PdCl₂dppf (312 mg, 0.38 mmol) in DMF (20 ml) were heated at 80° C. for 20 hrs. The cooled reaction was absorbed onto silica and applied to a bond-elut (silica, 10 g) and eluted with a cyclohexane/ethyl acetate gradient. The product fractions were concentrated under vacuum, dissolved in DMF (20 ml) and reacted with bis(pinnacolato)diboron (1.77 g, 7.0 mmol), potassium acetate (687 mg, 7.0 mmol) and PdCl₂dppf (143 mg, 0.175 mmol) at 80° C. for 16 hrs. The cooled reaction was absorbed onto silica and applied to a bond-elut (silica, 10 g) and eluted with a cyclohexane/ethyl acetate gradient. The product fractions were concentrated under vacuum to give N-[4-methyl-3-(4,4,5,5-tetramethyl-[1,3,2]dioxaborolan-2-yl)-phenyl]thiophene-3-amide. LCMS: retention time 3.65 min, MH⁺ 344. NMR: δH [²H₆]-DMSO 9.99,(1H, b), 8.35, (1H, s), 7.90,(1H, d), 7.85,(1H, dd), 7.63,(2H, m), 7.14,(1H, d), 2.42,(3H, s), 1.30,(12H, s).

Intermediate 15

N-(3-Iodo-4-methylphenyl)-3-furamide

3-Furoic acid (2.4 g, 21.45 mmol) and HATU (8.15 g, 21.45 mmol) in DMF (25 ml) were stirred at room temperature for 15 mins. HOBT (2.9 g, 21.45 mmol), 3-iodo-4-methylaniline (5.0 g, 21.45 mmol) and DIPEA (11.2 ml, 64.35 mmol) were added and the reaction stirred at room temperature for 16 hrs. The solvent was evaporated under vacuum and the residue partitioned between ethyl acetate (100 ml) and aqueous sodium carbonate (10%, 100 ml). The aqueous layer was extracted with ethyl acetate (50 ml) and the combined organic phases washed with hydrochloric acid (2N, 75 ml), water (75 ml) and brine (75 ml). The organic phase was dried (magnesium sulphate) and absorbed onto silica. The silica was applied to a flash silica column and eluted with cyclohexane/ethyl acetate (3:1). The solvent was evaporated from the product fractions under vacuum to give N-(3-iodo-4-methylphenyl)-3-furamide. LCMS: retention time 3.52 min, MH⁺ 328. NMR: δH [²H₆]-DMSO 9.92,(1H, b), 8.36,(1H, d), 8.23,(1H, d), 7.80,(1H, t), 7.66,(1H, dd), 7.29,(1H, d), 6.98, (1H, d), 2.33,(3H, s).

Intermediate 16

N-(3-Iodo-4-methylphenyl)thiophene-3-amide

Thiophene-3-carboxylic acid (2.75 g, 21.45 mmol) and HATU (8.15 g, 21.45 mmol) in DMF (25 ml) were stirred at room temperature for 15 mins. HOBT (2.9 g, 21.45 mmol), 3-iodo-4-methylaniline (5.0 g, 21.45 mmol) and DIPEA (11.2 ml, 64.35 mmol) were added and the reaction stirred at room temperature for 16 hrs. The solvent was evaporated under vacuum and the residue partitioned between ethyl acetate (100 ml) and aqueous sodium carbonate (10%, 100 ml). The aqueous layer was extracted with ethyl acetate (50 ml) and the combined organic phases washed with hydrochloric acid (2N, 75 ml), water (75 ml) and brine (75 ml). The organic phase was dried (magnesium sulphate) and absorbed onto silica. The silica was applied to a flash silica column and eluted with cyclohexane/ethyl acetate (4:1). The solvent was evaporated from the product fractions under vacuum to give N-(3-iodo-4-methylphenyl)thiophene-3-amide. LCMS: retention time 3.69 min, MH⁺ 344. NMR: δH [²H₆]-DMSO 10.06,(1H, b), 8.34,(1H, m), 8.29,(1H, d), 7.70,(1H, dd), 7.66,(1H, dd), 7.62,(1H, dd), 7.30,(1H, d), 2.34,(3H, s).

Intermediate 17

4-Methyl-3-(4,4,5,5-tetramethyl-[1,3,2]dioxaborolan-2-yl)benzoic acid

3-Iodo-4-methylbenzoic acid (10 g, 38.16 mmol), bis(pinnacolato)diboron (14.5 g, 57.24 mmol), potassium acetate (18.73 g, 190.8 mmol) and PdCl₂dppf (3.12 g, 3.8 mmol) in DMF (200 ml) were heated at 80° C. for 21 hrs. The solvent was evaporated from the cooled reaction under vacuum, the residue dissolved in ethyl acetate (300 ml) and hydrochloric acid (2N, 300 ml) and filtered through celite. The organic phase was separated and the aqueous extracted with ethyl acetate (2×300 ml). The combined organic extracts were washed with brine (500 ml) and dried (magnesium sulphate). The solvent was evaporated under vacuum and the residue absorbed onto silica and applied to a silica flash column. This was eluted with cyclohexane/ethyl acetate (5:1). The product fractions were concentrated under vacuum to give 4-methyl-3-(4,4,5,5-tetramethyl-[1,3,2]dioxaborolan-2-yl)benzoic acid. LCMS: retention time 3.65 min. NMR: δH [²H₆]-DMSO 12.83,(1H, b), 8.23,(1H, d), 7.89,(1H, dd), 7.29,(1H, d), 2.51,(3H, s), 1.30,(12H, s).

Intermediate 18

N-[4-Methyl-3-(4,4,5,5-tetramethyl-[1,3,2]dioxaborolan-2-yl)-phenyl]-2-pyrrolidin-1-yl-isonicotinamide Bis(pinacolato)diborane (7.24 g, 28.5 mmol) was added to a mixture of N-(3-iodo-4-methylphenyl)-2-pyrrolidin-1-yl-isonicotinamide (Intermediate 19) (7.73 g, 19 mmol) in dimethylformamide (100 ml) potassium acetate (9.32 g, 95 mmol) and PdCl₂dppf and the reaction was heated under an atmosphere of nitrogen at 80° C. for 16 hours. The reaction was cooled and the solvent removed in vacuo. The residue was taken up in chloroform (150 ml), washed with water (3×100 ml) and brine (100 ml), dried over magnesium sulfate, filtered and solvent removed in vacuo. The residue was purified by column chromatography (20:80 ethyl acetate: cyclohexane to 50:50 ethyl acetate: cyclohexane). To give N-[4-methyl-3-(4,4,5,5-tetramethyl-[1,3,2]dioxaborolan-2-yl)-phenyl]-2-pyrrolidin-1-yl-isonicotinamide as a white solid (1.5 g, 3.7 mmol). LCMS: retention time 2.90 min MH$^+$ 408. NMR: $\delta$H-CDCl$_3$ 8.27 (1H, d), 7.99 (1H, dd), 7.76 (1H, b), 7.65 (1H, d), 6.20 (1H, d), 6.82 (1H, b), 6.77 (1H, b), 3.52 (4H, apparent t), 2.52 (3H, s), 2.25 (4H, m).

Intermediate 19

N-(3-Iodo-4-methylphenyl)-2-pyrrolidin-1-yl-isonicotinamide

A solution of N-(3-iodo-4-methylphenyl)-2-chloro-isonicotinamide (Intermediate 20) (7.00 g, 18.8 mmol) in pyrrolidine (20 ml) was heated at 80° C. under an atmosphere of nitrogen for 16 hours. Excess pyrrolidine was removed in vacuo and the residue was titurated with dietheyl ether (20 ml). The resulting solid was collected by filtration and dried in vacuo to give N-(3-iodo-4-methylphenyl)-2-pyrrolidin-1-yl-isonicotinamide as a pale yellow solid (7.73 g, 18 mmol). LCMS: retention time 2.77 min MH$^{30}$ 408. NMR: $\delta$H [$^2$H$_6$]-DMSO 10.29 (1H, s), 8.29 (1H, d), 8.20 (1H, d), 7.71 (1H, dd), 7.72 (1H, dd), 6.97 (1H, brd), 6.88 (1H, b), 3.45 (2H, apparent t), 3.09 (2H, m), 2.35 (3H, s), 1.98 (2H, m), 1.82 (2H, m).

Intermediate 20

2-Chloro-N-(3-iodo-4-methylphenyl)-isonicotinamide

2-Chloroisonicotinic acid (3.3 g, 21 mmol), HATU (8.75 g, 23 mmol), diisopropylethyl amine (10.9 ml, 63 mmol) and 4-iodo-3-methylaniline (5.00 g, 21 mmol) in dimethylformamide (50 ml) were heated under nitrogen for 16 hours. The reaction was cooled, solvent removed in vacuo and the residue taken up in dichloromethane (150 ml). The organic solution was washed with water (3×100 ml) and brine (100 ml), dried over magnesium sulfate, filtered and solvent removed in vacuo. The residue was purified by column chromatography (40:60 ethyl acetate: cyclohexane) to give 2-chloro-N-(3-iodo-4-methylphenyl)-isonicotinamide as a white solid (7.00 g, 18.8 mmol). LCMS: retention time 3.59 min MH$^-$ 373. NMR: $\delta$H [$^2$H$_6$]-DMSO 10.52 (1H, s), 8.62 (1H, d), 8.29 (1H, d), 7.99 (1H, b), 7.87 (1H, dd), 7.70 (1H, dd), 7.34 (1H, d), 2.36 (3H, s).

Intermediate 21

6-Chloro-N-cyclopropylmethylnicotinamide

6-Bromonicotinic acid (200 mg, 0.99 mmol) was heated at reflux in thionyl chloride (2 ml) for 2.5 hrs. The reaction was allowed to cool to room temperature and the excess thionyl chloride evaporated under vacuum. The residue was dissolved in acetone (4 ml), cyclopropylmethylamine (71 mg, 0.10 mmol) and sodium carbonate (500 mg) were added to the solution. The reaction was stirred at room temperature for 4 hrs, filtered and the filtrate reduced to dryness under vacuum to give 6-chloro-N-cyclopropylmethylnicotinamide as a cream solid. NMR: $\delta$H [$^2$H$_6$]-DMSO 8.82,(2H, m), 8.23,(1H, dd), 7.63,(1H, d), 3.14,(2H, t), 1.01,(1H, m), 0.44,(2H, m), 0.22,(2H, m).

General Method A

6-Bromonicotinic acid (100 mg, 0.5 mmol) was heated at 95° C. in thionyl chloride (0.63 ml) for 2 hours. The excess thionyl chloride was evaporated under vacuum and the residue dissolved in DCM (2 ml). To this solution, amine (0.5 mmol) and sodium carbonate (100 mg) were added and the reaction was stirred at room temperature for 2 hours. The reaction was filtered and the residue washed with DCM. The combined filtrate and washings were reduced to dryness to give the desired 6-chloronicotinamide.

| Compound | Amine | MH$^+$ | Retention time (minutes) |
|---|---|---|---|
| Intermediate 22: 6-Chloro-N-(3-methylbutyl)nicotinamide | 3-methylbutylamine | 227 | 2.92 |
| Intermediate 23: 6-Chloro-N-(1-cyclopropylethyl)nicotinamide | 1-cyclopropylethylamine | 225 | 2.65 |
| Intermediate 24: 6-Chloro-N-(2,2-dimethylpropyl))nicotinamide | 2,2-dimethylpropylamine | 227 | 2.82 |
| Intermediate 25: 6-Chloro-N-(2,2-dimethylcyclopropyl)nicotinamide | 2,2-dimethylcyclopropylamine | 225 | 2.67 |
| Intermediate 26: 6-Chloro-N-cyclopropylnicotinamide | cyclopropylamine | 197 | 2.19 |
| Intermediate 27: 6-Chloro-N-cyclohexylmethylnicotinamide | cyclohexylmethylamine | 253 | 3.18 |
| Intermediate 28: 6-Chloro-N-cyclobutylnicotinamide | cyclobutylamine | 211 | 2.51 |
| Intermediate 29: 6-Chloro-N-(2-methylpropyl)nicotinamide | 2-methylpropylamine | 213 | 2.63 |
| Intermediate 30: 6-Chloro-N-propylnicotinamide | propylamine | 199 | 2.38 |
| Intermediate 31: 6-Chloro-N-cyclopentylnicotinamide | cyclopentylamine | 225 | 2.70 |

Intermediate 32

6-Chloro-N-cyclobutylmethylnicotinamide

6-Chloro-N-cyclobutylmethylnicotinamide was prepared from cyclobutylmethylamine using General Method A.
NMR: $\delta$H [$^2$H$_6$]-DMSO 8.81,(1H, d), 8.70,(1H, bt), 8.22,(1H, dd), 7.64,(1H, d), 3.91,(1H, 3.30,(2H, t), 2.52,(1H, m), 1.99,(2H, m), 1.81,(2H, m), 1.73,(2H, m).

Intermediate 33

6-Chloro-N-(1-methylpropyl)nicotinamide

6-Chloro-N-(1-methylpropyl)nicotinamide was prepared from 1-methylpropylamine using General Method A.
NMR: $\delta$H [$^2$H$_6$]-DMSO 8.82,(1H, d), 8.42,(1H, d), 8.24,(1H, dd), 7.64,(1H, d), 3.91,(1H, m), 1.51,(2H, m), 1.15,(3H, d), 0.87,(3H, t).

Intermediate 34

N-Cyclopropyl-5-fluoro-4-methyl-3-(4,4,5,5-tetramethyl-[1,3,2]dioxaborolan-2-yl)-benzamide 3-Bromo-N-cyclopropyl-5-fluoro-4-methylbenzamide (Intermediate 35, 900 mg), bispinnacolatodiboron (4.5 g), potassium acetate (2.1 g) and PdCl$_2$dppf (75 mg) were mixed in DMF (40 ml) and heated at 100° C. for 18 hours. The cooled reaction was absorbed onto silica and applied to SPE's (Si 2×10 g). The SPE's were eluted with an ethylacetate/cyclohexane gradient (0-6.25% ethylacetate). The solvent was evaporated from the product fractions under vacuum and the residue recrystallised from cyclohexane to give N-cyclopropyl-5-fluoro-4-methyl-3-(4,4,5,5-tetramethyl-[1,3,2]dioxaborolan-2-yl)-benzamide (260 mg).
LCMS: MH$^+$ 320, retention time 3.39 mins.

Intermediate 35

3-Bromo-N-cyclopropyl-5-fluoro-4-methylbenzamide

3-Fluoro-4-methylbenzoic acid (462 mg, 3.0 mmol) was added to a stirred mixture of bromine (2.31 ml, 45 mmol) and iron powder (252 mg, 4.5 mmol) under nitrogen. The reaction was stirred at 20° C. for 4 hours and then left to stand for 16 hours. Sodium thiosulphate solution (200 ml) was added and the product was extracted into ethyl acetate (3×150 ml). Ethyl acetate extracts were combined and evaporated in vacuo. The crude product (mixture of isomers) was dissolved in dimethylformamide (7 ml). Cyclopropylamine (208 µl, 3.0 mmol), HOBT (405 mg, 3.0 mmol), 1-(3-dimethylaminopropyl)-3-ethylcarbodiimide hydrochloride (575 mg, 3.0 mmol) and DIPEA (525 µl, 3.0 mmol) were added to the stirred solution. The reaction was stirred for 5 hours at 20° C. Solvent was removed in vacuo and the residue was partitioned between ethyl acetate and water. Combined ethyl acetate extracts were washed sequentially with aqueous sodium hydrogen carbonate and hydrochloric acid (0.5M), then dried (magnesium sulphate). The ethyl acetate was evaporated in vacuo and the residue was purified by silica biotage chromatography eluting with cyclohexane:ethyl acetate (6:1) to give 3-bromo-N-cyclopropyl-5-fluoro-4-methylbenzamide (359 mg, 44%).
NMR: δH-CDCl$_3$ 7.68,(1H, s), 7.39,(1H, d), 6.19,(1H, bs), 2.88,(1H, m), 2.36,(3H, d), 0.88,(2H, m), 0.63,(2H, m).
LCMS: MH$^-$ 272.

Intermediate 36

{5-[(Cyclopropylamino)carbonyl]-3-fluoro-2-methylphenyl}boronic acid

N-Cyclopropyl-5-fluoro-3-iodo-4-methylbenzamide (Intermediate 37, 5 g) in THF (75 ml) was cooled to 0° C. and sodium hydride (60%, 1.23 g) added portionwise over 10 minutes. Once effervescence had ceased the reaction was cooled to −75° C. and n-butyl lithium (1.6M in hexanes, 20 ml) added over 25 minutes maintaining a temperature of <−70° C. Triisopropyl borate (8 ml) was added to the reaction over 10 minutes and the reaction stirred at −70° C. for 4 hours. The reaction was quenched with water (20 ml) and the mixture allowed to warm to 5° C. The reaction was concentrated under vacuum and the residue partitioned between saturated ammonium chloride and ethyl acetate. The organic phase was washed with saturated ammonium chloride, brine, dried (sodium sulphate) and reduced to dryness under vacuum. The residue was dissolved in DCM/ethyl acetate and purified by column chromatography on silica eluting with an ethyl acetate/DCM gradient (5-100% ethyl acetate) and then methanol. The product fractions were combined and the solvent evaporated under vacuum to give {5-[(cyclopropylamino)carbonyl]-3-fluoro-2-methylphenyl}boronic acid.
LCMS MH$^+$ 238, retention time 2.19 min.

Intermediate 37

N-Cyclopropyl-5-fluoro-3-iodo-4-methylbenzamide

N-Iodosuccinimide (22.5 g) was added in portions to a solution of 3-fluoro-4-methylbenzoic acid (15.4 g) in trifluoromethanesulphonic acid (100 ml) at 0° C. over 3 hours and the reaction then allowed to warm to room temperature overnight. The reaction mixture was poured into ice/water (400 ml) and the precipitate filtered off and washed with water. The solid remaining was dissolved in ethyl acetate, washed with aqueous sodium thiosulphate (×2), then brine, dried (magnesium sulphate) and the solvent evaporated under vacuum. The residue was mixed with thionyl chloride (30 ml) and heated at 100° C. for 2.5 hours. The excess thionyl chloride was removed from the cooled reaction under vacuum and the residue dissolved in DCM (100 ml). Sodium carbonate (25 g) and cyclopropylamine (13 ml) were added to the solution and the reaction stirred at room temperature for 72 hours. The reaction was filtered and the residue washed with DCM and ethyl acetate. The solvent was evaporated from the combined filtrate and washings under vacuum. The residue was absorbed onto silica and chromatographed on a flash silica column eluting with an ethyl acetate/cyclohexane gradient (22-28% ethyl acetate). Appropriate fractions were reduced to dryness under vacuum to give N-cyclopropyl-5-fluoro-3-iodo-4-methylbenzamide.
LCMS; MH+ 320, retention time 3.16 minutes.

Intermediate 38

6-{5-[(Cyclopropylamino)carbonyl]-3-fluoro-2-methylphenyl}nicotinic acid

N-Cyclopropyl-5-fluoro-4-methyl-3-(4,4,5,5-tetramethyl-[1,3,2]dioxaborolan-2-yl)-benzamide (3.2 g), methyl 6-chloronicotinate (1.73 g), tetrakis(triphenylphosphine)palladium (210 mg) and aqueous sodium hydrogen carbonate (1M, 30 ml) were mixed in propan-2-ol (100 ml) and heated at 90° C. for 18 hours. The reaction was allowed to cool and the propan-2-ol removed under vacuum. The residue was partitioned between ethyl acetate and aqueous sodiumhydrogen carbonate (1M). The aqueous phase was acidified with hydrochloric acid (2N) and extracted with ethyl acetate (×2). The organic extracts were washed with brine, dried (magnesium sulphate) and reduced to dryness under vacuum. The resulting foam was triturated with ether to give 6-{5-[(cyclopropylamino)carbonyl]-3-fluoro-2-methylphenyl}nicotinic acid as a solid.
LCMS: MH+315, retention time 2.87 mins.

Intermediate 39

(2-Ethylcyclopropyl)methylamine

A solution of 2-ethylcyclopropylcarboxamide (250 mg, 2.2 mmol) in THF was heated to reflux. Borane-dimethylsulphide (1M solution in DCM, 3.2 ml, 3.2 mmol) was added dropwise over 30 minutes and the reaction refluxed for 16 hours. Hydrochloric acid (6N, 0.5 ml) was added dropwise and the mixture heated at reflux for 30 minutes. The cooled reaction mixture was diluted with water (20 ml), washed with ether (50 ml) and basified with sodium hydroxide (6N). The aqueous was extracted with ether (50 ml×3) and ethyl acetate (50 ml). The combined organic extracts were dried (magnesium sulphate), acidified with hydrogen chloride (3.3M in methanol) and reduced to dryness under vacuum to give (2-ethylcyclopropyl)methylamine (230 mg).
NMR: δH [$^2$H$_6$]-DMSO 7.85,(3H, b), 2.66,(2H, d), 1.30-1.13,(2H, m), 0.91,(3H, t), 0.77-0.66,(2H, m), 0.46,(1H, m), 0.33,(1H, m).

General Method B

The 2-chloropyridine (0.05 mmol), phenyl pinnacolborane (0.05 mmol), tetrakis(triphenylphosphine) palladium (1 mg) and aqueous sodium carbonate (0.25 ml) in propan-2-ol (1 ml) were heated at 85° C. under nitrogen for 18 hours. The cooled reaction was diluted with ethyl acetate (4 ml) and methanol (2 ml) and filtered through an SCX bond-elut (1 g). The product was eluted with 10% ammonia (s.g. 0.88) in methanol. The solvents were evaporated and the residue triturated with ether.

Example 1

N-(3-[5-(Cyclopropylmethyl-carbamoyl)-pyridin-2-yl]-4-methyl-phenyl)-2-pyrrolidin-1-yl-isonicotinamide

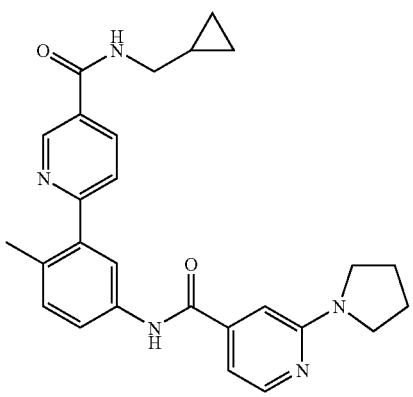

6-Chloro-N-cyclopropylmethylnicotinamide (Intermediate 1) (25 mg, 0.098 mmol) and N-[4-methyl-3-(4,4,5,5-tetramethyl-[1,3,2]dioxaborolan-2-yl)-phenyl]-2-pyrrolidin-1yl-isonicotinamide (Intermediate 18) (30 mg, 0.074 mmol), aqueous sodium carbonate (2N, 0.5 ml) and tetrakis(triphenylphosphine)palladium (4 mg) were heated at 80° C. in DMF (1 ml) for 18 hours. The reaction was absorbed onto silica,applied to a bond-elut (10 g, silica) and eluted with an ethylacetate/cyclohexane (0 to 100%), then acetone and methanol. The solvent was evaporated from the product fractions under vacuum and the residue triturated with ether to give N-(3-[5-(cyclopropylmethyl-carbamoyl)-pyridin-2-yl]-4-methyl-phenyl)-2-pyrrolidin-1-yl-isonicotinamide as a white solid (20 mg). LCMS: retention time 2.42 min, MH+ 456. NMR: δH [$^2$H$_6$]-DMSO 10.32,(1H, s), 9.09,(1H, s), 8.82,(1H, t), 8.28,(1H, m), 8.19,(1H, m), 7.85,(1H, t), 7.76,(1H, m), 7.64,(1H, m), 7.31,(1H, m), 6.98,(1H, m), 6.88,(1H, s), 3.43,(4H, m), 3.18,(2H, m), 2.31,(3H, s), 1.95,(4H, m), 1.07,(1H, m), 0.45,(2H, m), 0.25,(2H, m).

Example 2

N-Cyclopropylmethyl-6-[2-methyl-5-(3-pyridin-2-yl-phenylcarbamoyl)-phenyl]-nicotinamide

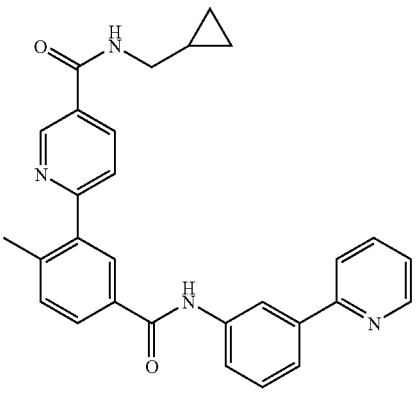

6-Chloro-N-cyclopropylmethylnicotinamide (Intermediate 1) (18.5 mg, 0.073 mmol) and 4-methyl-N-(3-pyridin-2-yl-phenyl)-3-(4,4,5,5-tetramethyl-[1,3,2]dioxaborolan-2-yl)-benzamide (Intermediate 6) (30 mg, 0.072 mmol), aqueous sodium carbonate (2N, 0.5 ml) and tetrakis(triphenylphosphine)palladium (4 mg) were heated at 90° C. in DMF (1 ml) for 4 hours. The reaction was absorbed onto silica, applied to a bond-elut (5 g, silica) and eluted with an ethylacetate/cyclohexane (0 to 100%) and then acetone. The solvent was evaporated from the product fractions under vacuum and the residue triturated with ether to give N-cyclopropylmethyl-6-[2-methyl-5-(3-pyridin-2-yl-phenylcarbamoyl)-phenyl]-nicotinamide as a white solid (20 mg). LCMS: retention time 3.18 min, MH− 463. NMR: δH [$^2$H$_6$]-DMSO 10.43,(1H, s), 9.14,(1H, s), 8.86,(1H, t), 8.69,(1H, s), 8.53,(1H, s), 8.34,(1H, d), 8.11,(1H, s), 8.01,(1H, d), 7.95-7.89,(3H, m), 7.81-7.78,(2H, m), 7.53-7.46,(2H, m), 7.38,(1H, t), 3.21,(2H, t), 2.44,(3H, s), 1.07,(1H, m), 0.47,(2H, m), 0.27,(2H, m).

Example 3

6-(5-Cyclopropylcarbamoyl-2-methyl-phenyl)-N-cyclopropylmethyl-nicotinamide

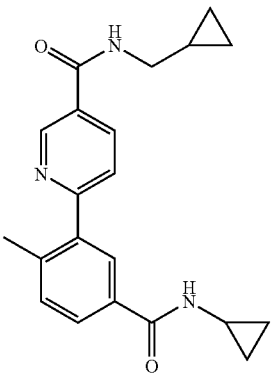

6-Chloro-N-cyclopropylmethylnicotinamide (Intermediate 1) (25.5 mg, 0.10 mmol) and N-cyclopropyl-4-methyl-3-(4,4,5,5-tetramethyl-[1,3,2]dioxaborolan-2-yl)-benzamide (Intermediate 8) (30 mg, 0.10 mmol), aqueous sodium carbonate (2N, 0.5 ml) and tetrakis(triphenylphosphine)palladium (4 mg) were heated at 90° C. in DMF (1 ml) for 3 hours. The reaction was absorbed onto silica, applied to a bond-elut (5 g, silica) and eluted with an ethylacetate/cyclohexane (0 to 100%) and then acetone. The solvent was evaporated from the product fractions under vacuum and the residue triturated with ether to 6-(5-cyclopropylcarbamoyl-2-methyl-phenyl)-N-cyclopropylmethyl-nicotinamide as a cream solid. LCMS: retention time 2.70 min, MH+ 350. NMR: δH [$^2$H$_6$]-DMSO 9.11,(1H, s), 8.84,(1H, t), 8.48,(1H, d), 8.31,(1H, dd), 7.88,(1H, s), 7.81,(1H, d), 7.70,(1H, d), 7.41,(1H, d), 3.20,(1H, t), 2.86,(1H, m), 2.37,(3H, s), 1.06,(1H, m), 0.69,(2H, m), 0.57,(2H, m), 0.46,(2H, m), 0.26,(2H, m).

Example 4

N-Cyclopropylmethyl-6-[5-(thiadiazol-2-ylcarbamoyl)-2-methyl-phenyl]-nicotinamide

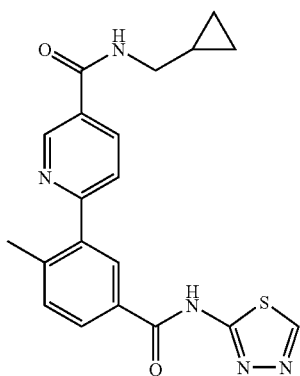

N-Cyclopropylmethyl-6-[5-(thiadiazol-2-ylcarbamoyl)-2-methyl-phenyl]-nicotinamide was prepared from 6-chloro-N-cyclopropylmethylnicotinamide (Intermediate 1) and 4-methyl-3-(4,4,5,5-tetramethyl-[1,3,2]dioxaborolan-2-yl)-N-(thiadiazol-2-yl)-benzamide (Intermediate 12) using General Method B. LCMS: retention time 2.79 min, MH⁻ 394. NMR: δH [$^2$H$_6$]-DMSO 13.14,(1H, b), 9.24,(1H, s), 9.14,(1H, s), 8.86,(1H, t), 8.35,(1H, d), 8.25,(1H, s), 8.10,(1H, d), 7.82,(1H, d), 7.54,(1H, d), 3.21,(2H, t), 2.46,(3H, s), 1.07,(1H, m), 0.47,(2H, m), 0.27,(2H, m).

Example 5

N-Cyclopropylmethyl-6-[5-(thiazol-2-ylcarbamoyl)-2-methyl-phenyl]-nicotinamide

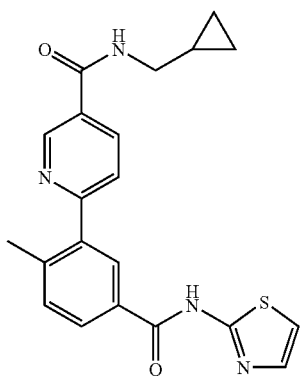

N-Cyclopropylmethyl-6-[5-(thiazol-2-ylcarbamoyl)-2-methyl-phenyl]-nicotinamide was prepared from 6-chloro-N-cyclopropylmethylnicotinamide (Intermediate 1) and 4-methyl-3-(4,4,5,5-tetramethyl-[1,3,2]dioxaborolan-2-yl)-N-(thiazol-2-yl)-benzamide (Intermediate 11) using General Method B. LCMS: retention time 2.99 min, MH⁻ 393. NMR: δH [$^2$H$_6$]-DMSO 12.71,(1H, b), 9.13,(1H, s), 8.86,(1H, t), 8.34,(1H, d), 8.21,(1H, s), 8.07,(1H, d), 7.81,(1H, d), 7.57,(1H, d), 7.52,(1H, d), 7.29,(1H, d), 3.21,(2H, t), 2.45,(3H, s), 1.07,(1H, m), 0.47,(2H, m), 0.27,(2H, m).

Example 6

6-[5-(Cyclopropylmethylcarbamoyl)-2-methyl-phenyl]-N-cyclopropylmethyl-nicotinamide

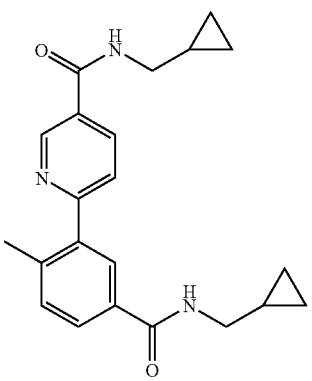

6-[5-(Cyclopropylmethyl)carbamoyl-2-methyl-phenyl]-N-cyclopropylmethyl-nicotinamide was prepared from 6-chloro-N-cyclopropylmethylnicotinamide (Intermediate 1) and N-(cyclopropylmethyl)-4-methyl-3-(4,4,5,5-tetramethyl-[1,3,2]dioxaborolan-2-yl)-benzamide (Intermediate 10) using General Method B. LCMS: retention time 2.87 min, MH⁻ 364. NMR: δH [$^2$H$_6$]-DMSO 9.10,(1H, s), 8.83,(1H, t), 8.60,(1H, t), 8.30,(1H, dd), 7.92,(1H, s), 7.84,(1H, d), 7.71,(1H, d), 7.41,(1H, d), 3.19,(2H, t), 3.13,(2H, t), 2.37,(3H, s), 1.03,(2H, m), 0.44,(4H, m), 0.23,(4H, m).

Example 7

N-Cyclopropylmethyl-6-[5-(fur-3-ylcarbonylamino)-2-methyl-phenyl]-nicotinamide

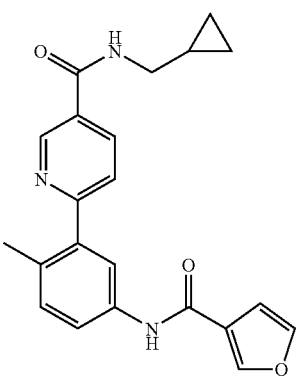

N-Cyclopropylmethyl-6-[5-(fur-3-ylcarbonylamino)-2-methyl-phenyl]-nicotinamide was prepared from 6-chloro-N-cyclopropylmethylnicotinamide (Intermediate 1) and N-[4-methyl-3-(4,4,5,5-tetramethyl-[1,3,2]dioxaborolan-2-yl)-phenyl]-3-furamide (Intermediate 13) using General Method B. LCMS: retention time 2.96 min, MH⁻ 376. NMR: δH [$^2$H$_6$]-DMSO 9.99,(1H, s), 9.10,(1H, s), 8.83,(1H, t), 8.38,(1H, s), 8.30,(1H, d), 7.80,(2H, s), 7.75,(1H, d), 7.66,(1H, d), 7.30,(1H, d), 3.20,(2H, t), 2.31,(3H, s), 1.06,(1H, m), 0.46,(2H, m), 0.27,(2H, m).

Example 8

N-Cyclopropylmethyl-6-[2-methyl-5-(thiophen-3-ylcarbonylamino)-phenyl]-nicotinamide

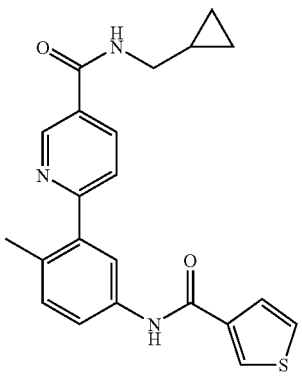

N-Cyclopropylmethyl-6-[2-methyl-5-(thiophen-3-ylcarbonylamino)-phenyl]-nicotinamide was prepared from 6-chloro-N-cyclopropylmethylnicotinamide (Intermediate 1) and N-[4-methyl-3-(4,4,5,5-tetramethyl-[1,3,2]dioxaborolan-2-yl)-phenyl]thiophene-3-amide (Intermediate 14) using General Method B. LCMS: retention time 3.07 min, MH⁻ 392. NMR: δH [²H₆]-DMSO 10.11,(1H, s), 9.11,(1H, s), 8.83,(1H, t), 8.35,(1H, s), 8.30,(1H, dd), 7.85,(1H, s), 7.78,(1H, d), 7.67-7.63,(3H, m), 7.31,(1H, d), 3.20,(2H, t), 2.31,(3H, s), 1.06,(1H, m), 0.46,(1H, m), 0.27,(1H, m).

Example 9

6-(5-Cyclopropylcarbamoyl-2-methyl-phenyl)-N-(4-methoxyphenyl)-nicotinamide

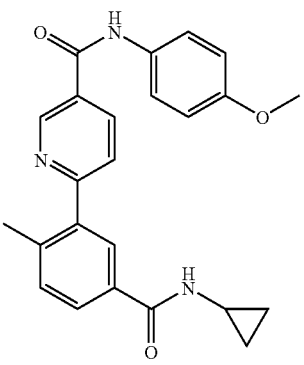

6-[5-Cyclopropylcarbamoyl-2-methyl-phenyl]-N-(4-methoxyphenyl)-nicotinamide was prepared from 6-chloro-N-(4-methoxyphenyl)nicotinamide (Intermediate 2) and N-cyclopropyl-4-methyl-3-(4,4,5,5-tetramethyl-[1,3,2]dioxaborolan-2-yl)-benzamide (Intermediate 8) using General Method B. LCMS: retention time 2.96 min, MH⁺ 402.
NMR: δH [²H₆]-DMSO 10.38,(1H, s), 9.20,(1H, s), 8.49,(1H, d), 8.40,(1H, dd), 7.91,(1H, s), 7.82,(1H, d), 7.76,(1H, d), 7.71,(2H, d), 7.43,(1H, d), 6.96,(2H, d), 3.76,(3H, s), 2.87,(1H, m), 2.40,(3H, s), 0.70,(2H, m), 0.58,(2H, m).

Example 10

N-(4-Methoxyphenyl)-6-[2-methyl-5-(thiadiazol-2-ylcarbamoyl)-phenyl]-nicotinamide

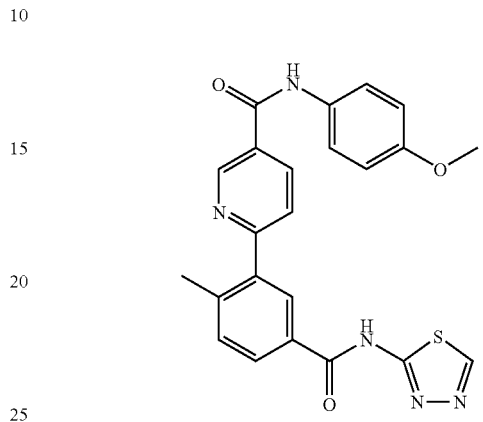

N-(4-Methoxyphenyl)-6-[2-methyl-5-(thiadiazol-2-ylcarbamoyl)-phenyl]-nicotinamide was prepared from 6-chloro-N-(4-methoxyphenyl)nicotinamide (Intermediate 2) and 4-methyl-3-(4,4,5,5-tetramethyl-[1,3,2]dioxaborolan-2-yl)-N-(thiadiazol-2-yl)-benzamide (Intermediate 12) using General Method B. LCMS: retention time 3.05 min, MH⁻ 446. NMR: δH [²H₆]-DMSO 13.15,(1H, b), 10.41,(1H, s), 9.24,(2H, m), 8.45,(1H, dd), 8.28,(1H, s), 8.11,(1H, d), 7.88,(1H, d), 7.71,(2H, d), 7.56,(1H, d), 6.97,(2H, d), 3.76,(3H, s), 2.48,(3H, s).

Example 11

N-(4-Methoxyphenyl)-6-[2-methyl-5-(thiazol-2-ylcarbamoyl)-phenyl]-nicotinamide

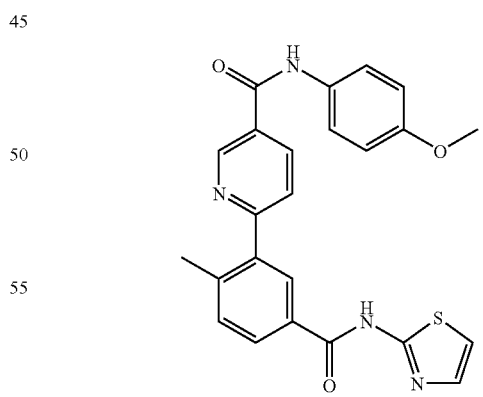

N-(4-Methoxyphenyl)-6-[2-methyl-5-(thiazol-2-ylcarbamoyl)-phenyl]-nicotinamide was prepared from 6-chloro-N-(4-methoxyphenyl)nicotinamide (Intermediate 2) and 4-methyl-3-(4,4,5,5-tetramethyl-[1,3,2]dioxaborolan-2-yl)-N-(thiazol-2-yl)-benzamide (Intermediate 11) using General Method B. LCMS: retention time 3.22 min, MH⁻ 445. NMR: δH [²H₆]-DMSO 12.72,(1H, s), 10.40,(1H, s), 9.22,(1H, d), 8.44,(1H, dd), 8.24,(1H, s), 8.09,(1H, d), 7.87,(1H, d), 7.71,(2H, d), 7.58,(1H, d), 7.53,(1H, d), 7.30,(1H, d), 6.97,(2H, d), 3.76,(3H, s), 2.48,(3H, s).

Example 12

6-(5-Cyclopropylmethylcarbamoyl-2-methyl-phenyl)-N-(4-methoxyphenyl)-nicotinamide

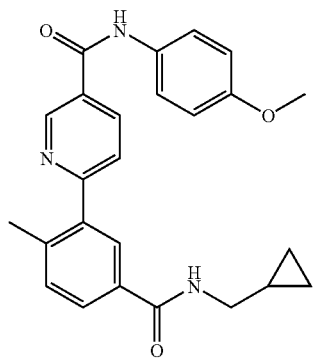

6-[5-Cyclopropylmethylcarbamoyl-2-methyl-phenyl]-N-(4-methoxyphenyl)-nicotinamide was prepared from 6-chloro-N-(4-methoxyphenyl)nicotinamide (Intermediate 2) and N-cyclopropylmethyl-4-methyl-3-(4,4,5,5-tetramethyl-[1,3,2]dioxaborolan-2-yl)-benzamide (Intermediate 10) using General Method B. LCMS: retention time 3.12 min, MH⁻ 416. NMR: δH [²H₆]-DMSO 10.39,(1H, s), 9.21,(1H, d), 8.63,(1H, t), 8.41,(1H, dd), 7.96,(1H, s), 7.86,(1H, d), 7.79,(1H, d), 7.71,(2H, d), 7.44,(1H, d), 6.96,(2H, d), 3.76,(3H, s), 3.15,(2H, t), 2.41,(3H, s), 1.03,(1H, m), 0.43,(2H, m), 0.23,(2H, m).

Example 13

6-[5-(Fur-3-ylcarbonylamino)-2-methyl-phenyl]-N-(4-methoxyphenyl)-nicotinamide

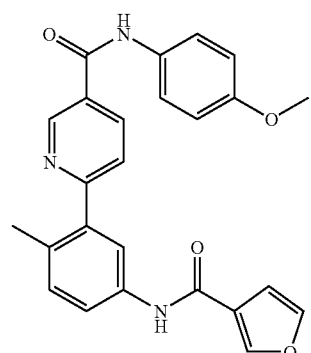

6-[5-(Fur-3-ylcarbonylamino)-2-methyl-phenyl]-N-(4-methoxyphenyl)-nicotinamide was prepared from 6-chloro-N-(4-methoxyphenyl)nicotinamide (Intermediate 2) and N-[4-methyl-3-(4,4,5,5-tetramethyl-[1,3,2]dioxaborolan-2-yl)-phenyl]-3-furamide (Intermediate 13) using General Method B. LCMS: retention time 3.19 min, MH⁻ 428. NMR: δH [²H₆]-DMSO 10.38,(1H, s), 10.00,(1H, s), 9.19,(1H, s), 8.38,(2H, m), 7.83,(1H, s), 7.80,(1H, s), 7.76,(1H, s), 7.73-7.69,(3H, m), 7.32,(1H, s), 7.01,(1H, s), 6.96,(2H, d), 3.76,(3H, s), 2.34,(3H, s).

Example 14

6-(5-Cyclopropylcarbamoyl-2-methyl-phenyl)-N-(3-methoxybenzyl)-nicotinamide

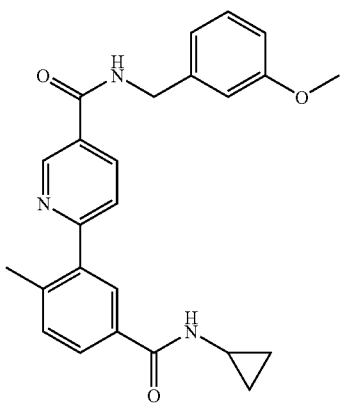

6-[5-Cyclopropylcarbamoyl-2-methyl-phenyl]-N-(3-methoxybenzyl)-nicotinamide was prepared from 6-chloro-N-(3-methoxybenzyl)nicotinamide (Intermediate 3) and N-cyclopropyl-4-methyl-3-(4,4,5,5-tetramethyl-[1,3,2]dioxaborolan-2-yl)-benzamide (Intermediate 8) using General Method B. LCMS: retention time 2.94 min, MH⁺ 416. NMR: δH [²H₆]-DMSO 9.29,(1H, t), 9.15,(1H, s), 8.48,(1H, d), 8.35,(1H, d), 7.89,(1H, s), 7.81,(1H, d), 7.72,(1H, d), 7.41,(1H, d), 7.26,(1H, t), 6.93,(2H, m), 6.84,(1H, s), 4.51,(2H, d), 3.75,(3H, s), 2.86,(1H, m), 2.38,(3H, s), 0.69,(2H, m), 0.57,(2H, m).

Example 15

N-(3-Methoxybenzyl)-6-[2-methyl-5-(thiadiazol-2-ylcarbamoyl)-phenyl]-nicotinamide

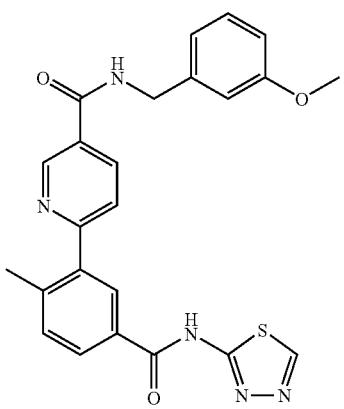

N-(3-Methoxybenzyl)-6-[2-methyl-5-(thiadiazol-2-ylcarbamoyl)-phenyl]-nicotinamide was prepared from 6-chloro-N-(3-methoxybenzyl)nicotinamide (Intermediate 3) and 4-methyl-3-(4,4,5,5-tetramethyl-[1,3,2]dioxaborolan-2-yl)-N-(thiadiazol-2-yl)-benzamide (Intermediate 12) using General Method B. LCMS: retention time 3.02 min, M⁻ 460. NMR: δH [²H₆]-DMSO 13.14,(1H, b), 9.32,(1H, t), 9.24, (1H, s), 9.18,(1H, d), 8.40,(1H, dd), 8.26,(1H, s), 8.10,(1H, d), 7.84,(1H, d), 7.55,(1H, d), 7.27,(1H, t), 6.94,(2H, m), 6.84,(1H, d), 4.53,(2H, d), 3.75,(3H, s), 2.46,(3H, s).

Example 16

N-(3-Methoxybenzyl)-6-[2-methyl-5-(thiazol-2-yl-carbamoyl)-phenyl]-nicotinamide

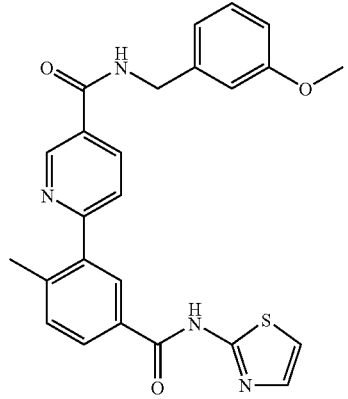

N-(3-Methoxybenzyl)-6-[2-methyl-5-(thiazol-2-ylcarbamoyl)-phenyl]-nicotinamide was prepared from 6-chloro-N-(3-methoxybenzyl)nicotinamide (Intermediate 3) and 4-methyl-3-(4,4,5,5-tetramethyl-[1,3,2]dioxaborolan-2-yl)-N-(thiazol-2-yl)-benzamide (Intermediate 11) using General Method B. LCMS: retention time 3.20 min, MH 459. NMR: δH [²H₆]-DMSO 12.71,(1H, b), 9.31,(1H, t), 9.17,(1H, d), 8.39,(1H, dd), 8.22,(1H, s), 8.07,(1H, d), 7.83,(1H, d), 7.57, (1H, d), 7.52,(1H, d), 7.29-7.25,(2H, m), 6.94,(2H, m), 6.84, (1H, d), 4.52,(2H, d), 3.75,(3H, s), 2.45,(3H, s).

Example 17

6-(5-Cyclopropylmethylcarbamoyl-2-methyl-phenyl)-N-(3-methoxybenzyl)-nicotinamide

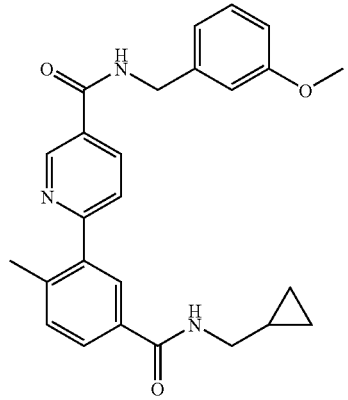

6-[5-Cyclopropylmethylcarbamoyl-2-methyl-phenyl]-N-(3-methoxybenzyl)-nicotinamide was prepared from 6-chloro-N-(3-methoxybenzyl)nicotinamide (Intermediate 3) and N-cyclopropylmethyl-4-methyl-3-(4,4,5,5-tetram-ethyl-[1,3,2]dioxaborolan-2-yl)-benzamide (Intermediate 10) using General Method B. LCMS: retention time 3.07 min, MH⁻ 430. NMR: δH [²H₆]-DMSO 9.30,(1H, t), 9.16,(1H, d), 8.62,(1H, t), 8.36,(1H, dd), 7.94,(1H, s), 7.85,(1H, d), 7.74, (1H, d), 7.43,(1H, d), 7.27,(1H, t), 6.94-6.92,(2H, m), 6.84, (1H, d), 4.51,(2H, d), 3.75,(3H, s), 3.14,(2H, t), 2.39,(3H, s), 1.03,(1H, m), 0.43,(2H, m), 0.23,(2H, m).

Example 18

6-[5-(Fur-3-ylcarbonylamino)-2-methyl-phenyl]-N-(3-methoxybenzyl)-nicotinamide

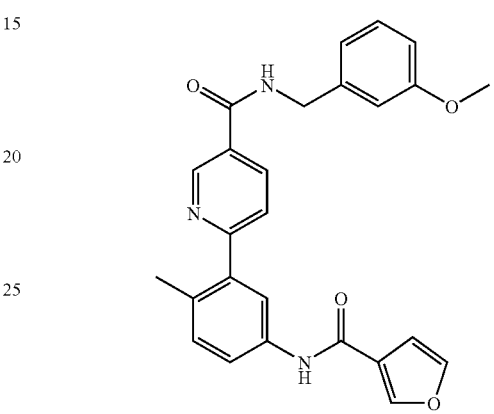

6-[5-(Fur-3-ylcarbonylamino)-2-methyl-phenyl]-N-(3-methoxybenzyl)-nicotinamide was prepared from 6-chloro-N-(3-methoxybenzyl)nicotinamide (Intermediate 3) and N-[4-methyl-3-(4,4,5,5-tetramethyl-[1,3,2]dioxaborolan-2-yl)-phenyl]-3-furamide (Intermediate 13) using General Method B. LCMS: retention time 3.17 min, MH 442. NMR: δH [²H₆]-DMSO 9.99,(1H, s), 9.29,(1H, t), 9.15,(1H, d), 8.38,(1H, s), 8.34,(1H, dd), 7.81,(2H, m), 7.75,(1H, d), 7.67, (1H, d), 7.31-7.25,(2H, m), 7.00.(1H, s), 6.94,(2H, m), 6.84, (1H, d), 4.51,(2H, d), 3.75,(3H, s), 2.32,(3H, s).

Example 19

N-(3-Methoxybenzyl)-6-[5-(thiophen-3-ylcarbonylamino)-2-methyl-phenyl]-nicotinamide

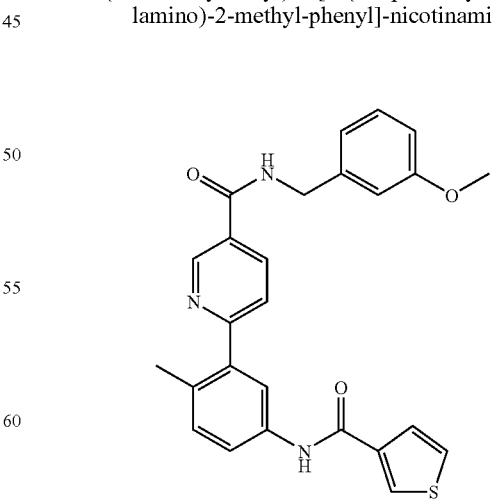

N-(3-Methoxybenzyl)-6-[5-(thiophen-3-ylcarbonylamino)-2-methyl-phenyl]-nicotinamide was prepared from 6-chloro-N-(3-methoxybenzyl)nicotinamide (Intermediate 3) and N-[4-methyl-3-(4,4,5,5-tetramethyl-[1,3,2]dioxaborolan-2-yl)-phenyl]thiophene-3-amide (Intermediate 14) using General Method B. LCMS: retention time 3.27 min, MH⁻ 458. NMR: δH [²H₆]-DMSO 10.12,(1H, s), 9.29,(1H, t), 9.15,(1H, d), 8.35-8.32,(2H, m), 7.86,(1H, s), 7.78,(1H, d), 7.68-7.65,(3H, m), 7.32-7.24,(2H, m), 6.94,(2H, m), 6.84, (2H, d), 4.51,(2H, d), 3.75,(3H, s), 2.32,(3H, s).

Example 20

6-(5-Cyclopropylcarbamoyl-2-methyl-phenyl)-N-(3-methylsulphonylaminobenzyl)-nicotinamide

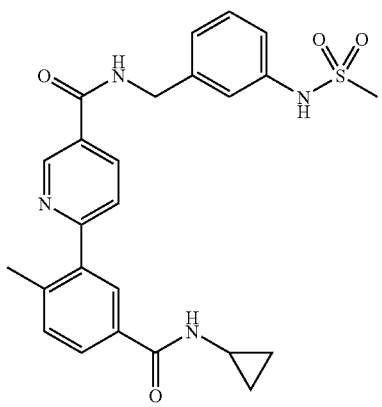

6-(5-Cyclopropylcarbamoyl-2-methyl-phenyl)-N-(3-methylsulphonylaminobenzyl)-nicotinamide was prepared from 6-chloro-N-(3-methylsulphonylaminobenzyl)nicotinamide (Intermediate 4) and N-cyclopropyl-4-methyl-3-(4,4,5,5-tetramethyl-[1,3,2]dioxaborolan-2-yl)-benzamide (Intermediate 8) using General Method B. LCMS: retention time 2.71 min, MH⁺ 479. NMR: δH [²H₆]-DMSO 9.33,(1H, t), 9.15, (1H, s), 8.48-8.33,(3H, m), 7.89,(1H, s), 7.81,(1H, d), 7.72, (1H, d), 7.41,(1H, d), 7.31,(1H, t), 7.21,(1H, s), 7.10,(2H, m), 4.51,(2H, d), 2.99,(3H, s), 2.86,(1H, m), 2.38,(3H, s), 0.69, (2H, m), 0.57,(2H, m).

Example 21

N-(3-Methylsulphonylaminobenzyl)-6-[2-methyl-5-(thiadiazol-2-ylcarbamoyl)-phenyl]-nicotinamide

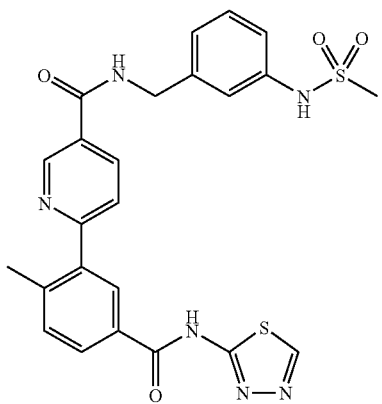

N-(3-Methylsulphonylaminobenzyl)-6-[2-methyl-5-(thiadiazol-2-ylcarbamoyl)-phenyl]-nicotinamide was prepared from 6-chloro-N-(3-methylsulphonylaminobenzyl)nicotinamide (Intermediate 4) and 4-methyl-3-(4,4,5,5-tetramethyl-[1,3,2]dioxaborolan-2-yl)-N-(thiadiazol-2-yl)-benzamide (Intermediate 12) using General Method B. LCMS: retention time 2.80 min, MH⁺ 523. NMR: δH [²H₆]-DMSO 9.35,(1H, t), 9.17,(2H, m), 8.38,(1H, d), 8.26,(1H, s), 8.09,(1H, d), 7.83,(1H, d), 7.52,(1H, d), 7.31,(1H, t), 7.22,(1H, s), 7.11, (2H, m), 4.52,(2H, d), 2.99,(3H, s), 2.46,(3H, s).

Example 22

N-(3-Methylsulphonylaminobenzyl)-6-[2-methyl-5-(thiazol-2-ylcarbamoyl)-phenyl]-nicotinamide

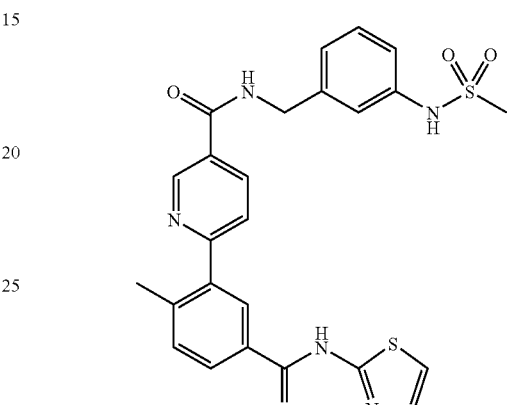

N-(3-Methylsulphonylaminobenzyl)-6-[2-methyl-5-(thiazol-2-ylcarbamoyl)-phenyl]-nicotinamide was prepared from 6-chloro-N-(3-methylsulphonylaminobenzyl)nicotinamide (Intermediate 4) and 4-methyl-3-(4,4,5,5-tetramethyl-[1,3,2]dioxaborolan-2-yl)-N-(thiazol-2-yl)-benzamide (Intermediate 11) using General Method B. LCMS: retention time 2.96 min, MH⁺ 522. NMR: δH [²H₆]-DMSO 10.19,(2H, b), 9.35,(1H, t), 9.17,(1H, s), 8.38,(1H, dd), 8.22,(1H, s), 8.07,(1H, d), 7.84,(1H, d), 7.57,(1H, d), 7.52,(1H, d), 7.31-7.28,(2H, m), 7.22,(1H, s), 7.11,(2H, m), 4.52,(2H, d), 2.99, (3H, s), 2.45,(3H, s).

Example 23

6-(5-Cyclopropylmethylcarbamoyl-2-methyl-phenyl)-N-(3-methylsulphonylaminobenzyl)-nicotinamide

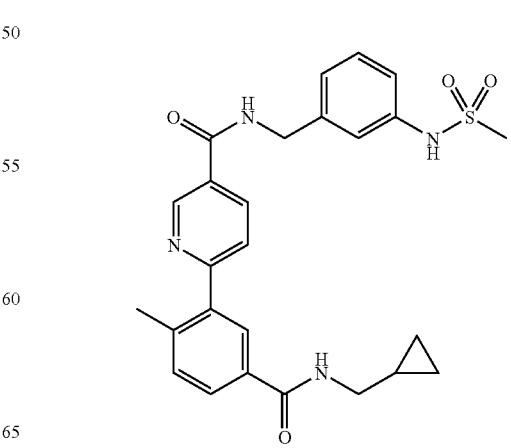

6-(5-Cyclopropylmethylcarbamoyl-2-methyl-phenyl)-N-(3-methylsulphonylaminobenzyl)-nicotinamide was prepared from 6-chloro-N-(3-methylsulphonylaminobenzyl)nicotinamide (Intermediate 4) and N-cyclopropylmethyl-4-methyl-3-(4,4,5,5-tetramethyl-[1,3,2]dioxaborolan-2-yl)-benzamide (Intermediate 10) using General Method B. LCMS: retention time 2.88 min, MH+ 493. NMR: δH [²H₆]-DMSO 9.34,(1H, t), 9.16,(1H, d), 8.96,(1H, b), 8.62,(1H, t), 8.35,(1H, dd), 7.94,(1H, s), 7.85,(1H, d), 7.75,(1H, d), 7.43,(1H, d), 7.31,(1H, t), 7.21,(1H, s), 7.11,(2H, m), 4.52,(2H, d), 3.14,(2H, t), 2.99,(3H, s), 2.39,(3H, s), 1.03,(1H, m), 0.43,(2H, m), 0.23,(2H, m).

Example 24

6-[5-(Fur-3-ylcarbonylamino)-2-methyl-phenyl]-N-(3-methylsulphonylaminobenzyl)-nicotinamide

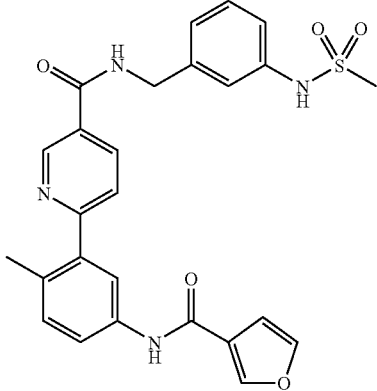

6-[5-(Fur-3-ylcarbonylamino)-2-methyl-phenyl]-N-(3-methylsulphonylaminobenzyl)-nicotinamide was prepared from 6-chloro-N-(3-methylsulphonylaminobenzyl)nicotinamide (Intermediate 4) and N-[4-methyl-3-(4,4,5,5-tetramethyl-[1,3,2]dioxaborolan-2-yl)-phenyl]-3-furamide (Intermediate 13) using General Method B. LCMS: retention time 2.93 min, MH+ 505. NMR: δH [²H₆]-DMSO 9.99,(1H, s), 9.32,(1H, t), 9.15,(1H, d), 8.95,(1H, b), 8.38,(1H, s), 8.33,(1H, dd), 7.81,(2H, d), 7.75,(1H, d), 7.68,(1H, d), 7.33-7.30,(2H, m), 7.21,(1H, s), 7.11,(2H, m), 7.01,(1H, s), 4.51,(2H, d), 2.99,(3H, s), 2.32,(3H, s).

Example 25

N-(3-Methylsulphonylaminobenzyl)-6-[5-(thiophen-3-ylcarbonylamino)-2-methyl-phenyl]-nicotinamide

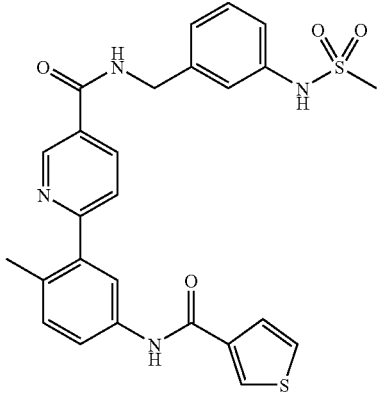

N-(3-Methylsulphonylaminobenzyl)-6-[5-(thiophen-3-ylcarbonylamino)-2-methyl-phenyl]-nicotinamide was prepared from 6-chloro-N-(3-methylsulphonylaminobenzyl)nicotinamide (Intermediate 4) and N-[4-methyl-3-(4,4,5,5-tetramethyl-[1,3,2]dioxaborolan-2-yl)-phenyl]thiophene-3-amide (Intermediate 14) using General Method B. LCMS: retention time 3.03 min, MH+ 521. NMR: δH [²H₆]-DMSO 10.12,(1H, s), 9.33,(1H, t), 9.15,(1H, s), 8.78,(1H, b), 8.36-8.32,(2H, m), 7.86,(1H, s), 7.78,(1H, d), 7.69-7.65,(3H, m), 7.31,(2H, m), 7.21,(1H, s), 7.11,(2H, m), 4.51,(2H, d), 2.99,(3H, s), 2.32,(3H, s).

Example 26

6-(5-Cyclopropylcarbamoyl-2-methyl-phenyl)-N-[2-(4-methylpiperazin-1-ylmethyl)phenyl]-nicotinamide

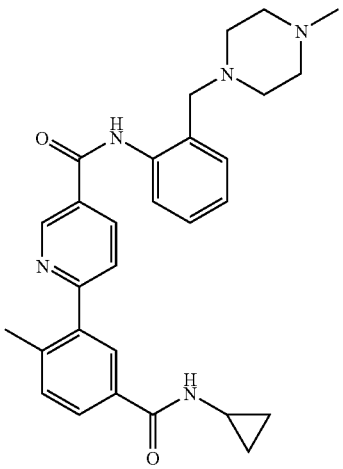

6-(5-Cyclopropylcarbamoyl-2-methyl-phenyl)-N-[2-(4-methylpiperazin-1-ylmethyl)phenyl]-nicotinamide was prepared from 6-chloro-N-[2-(4-methylpiperazin-1-ylmethyl)phenyl]nicotinamide (Intermediate 5) and N-cyclopropyl-4-methyl-3-(4,4,5,5-tetramethyl-[1,3,2]dioxaborolan-2-yl)-benzamide (Intermediate 8) using General Method B. LCMS: retention time 2.36 min, MH+ 484. NMR: δH [²H₆]-DMSO 11.70,(1H, b), 9.23,(1H, s), 8.50,(1H, d), 8.38,(1H, d), 8.33,(1H, d), 7.92,(1H, s), 7.83,(2H, m), 7.43,(1H, d), 7.36,(1H, t), 7.29,(1H, d), 7.11,(1H, t), 3.77,(2H, s), 2.87,(1H, m), 2.67-2.24,(11H, m), 2.13,(3H, s), 0.70,(2H, m), 0.58,(2H, m).

Example 27

N-[2-(4-Methylpiperazin-1-ylmethyl)phenyl]-6-[2-methyl-5-(thiadiazol-2-ylcarbamoyl)-phenyl]-nicotinamide

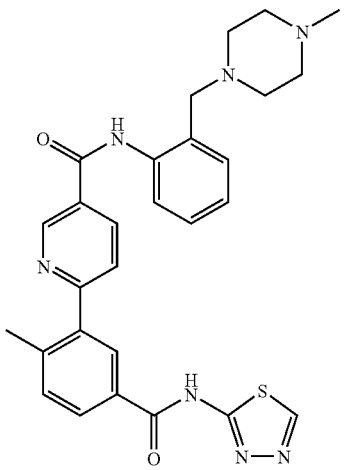

N-[2-(4-Methylpiperazin-1-ylmethyl)phenyl]-6-[2-methyl-5-(thiadiazol-2-ylcarbamoyl)-phenyl]-nicotinamide was prepared from 6-chloro-N-[2-(4-methylpiperazin-1-ylmethyl)phenyl]nicotinamide (Intermediate 5) and 4-methyl-3-(4,4,5,5-tetramethyl-[1,3,2]dioxaborolan-2-yl)-N-(thiadiazol-2-yl)-benzamide (Intermediate 12) using General Method B. LCMS: retention time 2.43 min, MH+ 528. NMR: δH [²H₆]-DMSO 13.07,(1H, b), 11.74,(1H, s), 9.26,(1H, s), 9.21,(1H, s), 8.43,(1H, d), 8.34,(1H, d), 8.29,(1H, s), 8.12,(1H, d), 7.93,(1H, d), 7.56,(1H, d), 7.36,(1H, t), 7.29,(1H, d), 7.11,(1H, t), 3.78,(2H, s), 2.67-2.26,(11H, m), 2.11,(3H, s).

Example 28

N-[2-(4-Methylpiperazin-1-ylmethyl)phenyl]-6-[2-methyl-5-(thiazol-2-ylcarbamoyl)-phenyl]-nicotinamide

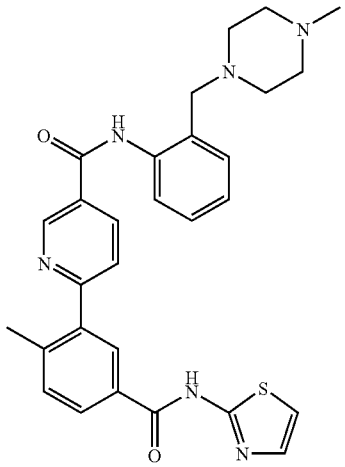

N-[2-(4-Methylpiperazin-1-ylmethyl)phenyl]-6-[2-methyl-5-(thiazol-2-ylcarbamoyl)-phenyl]-nicotinamide was prepared from 6-chloro-N-[2-(4-methylpiperazin-1-ylmethyl)phenyl]nicotinamide (Intermediate 5) and 4-methyl-3-(4,4,5,5-tetramethyl-[1,3,2]dioxaborolan-2-yl)-N-(thiazol-2-yl)-benzamide (Intermediate 11) using General Method B. LCMS: retention time 2.53 min, MH¹ 527. NMR: δH [²H₆]-DMSO 12.73,(1H, b), 11.70,(1H, b), 9.26,(1H, d), 8.43,(1H, dd), 8.33,(1H, d), 8.25,(1H, s), 8.10,(1H, d), 7.93,(1H, d), 7.58,(1H, d), 7.54,(1H, d), 7.36,(1H, t), 7.30,(2H, m), 7.12,(1H, t), 3.78,(2H, s), 2.67-2.25,(11H, b), 2.14,(3H, s).

Example 29

6-(5-Cyclopropylmethylcarbamoyl-2-methyl-phenyl)-N-[2-(4-methylpiperazin-1-ylmethyl)phenyl]-nicotinamide

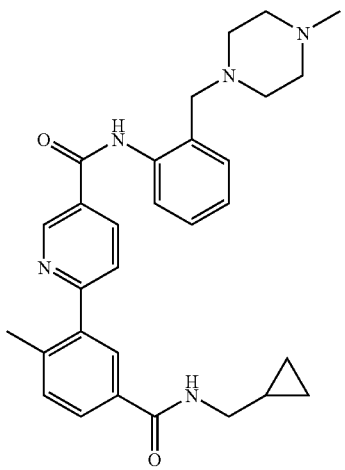

6-(5-Cyclopropylmethylcarbamoyl-2-methyl-phenyl)-N-[2-(4-methylpiperazin-1-ylmethyl)phenyl]-nicotinamide was prepared from 6-chloro-N-[2-(4-methylpiperazin-1-ylmethyl)phenyl]nicotinamide (Intermediate 5) and N-cyclopropylmethyl-4-methyl-3-(4,4,5,5-tetramethyl-[1,3,2]dioxaborolan-2-yl)-benzamide (Intermediate 10) using General Method B. LCMS: retention time 2.46 min, MH+ 498. NMR: δH [²H₆]-DMSO 11.67,(1H, b), 9.24,(1H, s), 8.63,(1H, t), 8.39,(1H, d), 8.32,(1H, d), 7.97,(1H, s), 7.88-7.82,(2H, m), 7.45,(1H, d), 7.36,(1H, t), 7.30,(1H, d), 7.11,(1H, t), 3.77,(2H, s), 3.15,(2H, t), 2.70-2.21,(11H, m), 1.04,(1H, m), 0.43,(2H, m), 0.23,(2H, m).

Example 30

6-[5-(Fur-3-ylcarbonylamino)-2-methyl-phenyl]-N-[2-(4-methylpiperazin-1-ylmethyl)phenyl]-nicotinamide

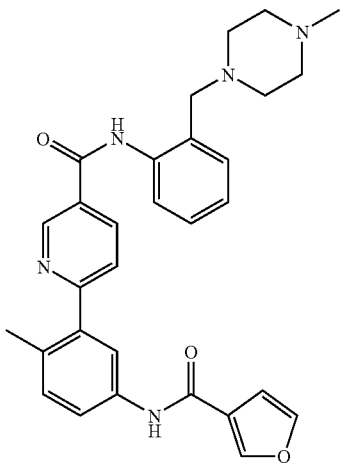

6-[5-(Fur-3-ylcarbonylamino)-2-methyl-phenyl]-N-[2-(4-methylpiperazin-1-ylmethyl)phenyl]-nicotinamide was prepared from 6-chloro-N-[2-(4-methylpiperazin-1-ylmethyl)phenyl]nicotinamide (Intermediate 5) and N-[4-methyl-3-(4,4,5,5-tetramethyl-[1,3,2]dioxaborolan-2-yl)-phenyl]-3-furamide (Intermediate 13) using General Method B. LCMS: retention time 2.53 min, MH+ 510. NMR: δH [²H₆]-DMSO 11.64,(1H, b), 10.02,(1H, s), 9.23,(1H, s), 8.38,(2H, m), 8.31,(1H, d), 7.86,(1H, s), 7.80,(1H, s), 7.76,(2H, m), 7.38-7.29,(3H, m), 7.11,(1H, t), 7.01,(1H, s), 3.77,(2H, s), 2.66-2.20,(11H, m), 2.16,(3H, s).

Example 31

N-[2-(4-Methylpiperazin-1-ylmethyl)phenyl]-6-[5-(thiophen-3-ylcarbonylamino)-2-methyl-phenyl]-nicotinamide

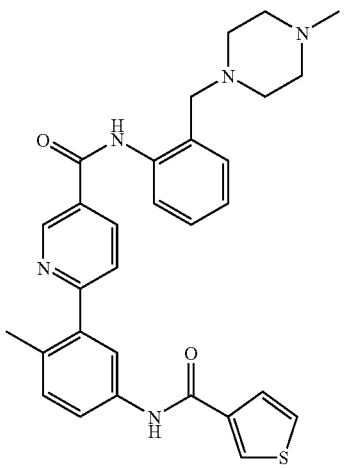

N-[2-(4-Methylpiperazin-1-ylmethyl)phenyl]-6-[5-(thiophen-3-ylcarbonylamino)-2-methyl-phenyl]-nicotinamide was prepared from 6-chloro-N-[2-(4-methylpiperazin-1-ylmethyl)phenyl]nicotinamide (Intermediate 5) and N-[4-methyl-3-(4,4,5,5-tetramethyl-[1,3,2]dioxaborolan-2-yl)-phenyl]thiophene-3-amide (Intermediate 14) using General Method B. LCMS: retention time 2.58 min, MH+ 526. NMR: δH [$^2$H$_6$]-DMSO 11.64,(1H, b), 10.14,(1H, s), 9.23,(1H, s), 8.38,(2H, m), 8.31,(1H, d), 7.91,(1H, s), 7.79-7.75,(2H, m), 7.65,(2H, m), 7.38-7.29,(3H, m), 7.11,(1H, t), 3.77,(2H, s), 2.67-2.24,(11H, m), 2.16,(3H, m).

General Method C

The 6-chloronicotinamide (25 mg), N-cyclopropyl-5-fluoro-4-methyl-3-(4,4,5,5-tetramethyl-[1,3,2]dioxaborolan-2-yl)-benzamide (Intermediate 34, 15 mg), tetrakis(triphenylphosphino)palladium (2 mg) and aqueous sodium hydrogen carbonate (1M, 0.5 ml) were mixed in propan-2-ol (2 ml) and heated at reflux for 18 hours. The propan-2-ol was evaporated and the residue diluted with ethylacetate/cyclohexane (1:2). The solution was applied to a SPE (Si, 2 g) and eluted with ethylacetate/cyclohexane (1:2) and then ethylacetate. The solvent was evaporated from the ethylacetate fraction and the residue triturated with ether to give the desired product as a white solid.

Examples 32 to 44 may also be prepared using {5-[(cyclopropylamino)carbonyl]-3-fluoro-2-methylphenyl}boronic acid (Intermediate 36) in place of Intermediate 34.

| Compound | Structure | 6-Chloronicotinamide | MH+ | Retention time (minutes) |
|---|---|---|---|---|
| Example 32 6-(5-Cyclopropylcarbamoyl-3-fluoro-2-methyl-phenyl)-N-cyclopropylmethyl-nicotinamide | 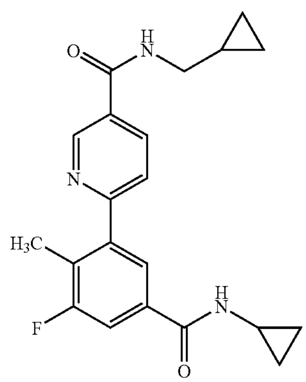 | 6-Chloro-N-cyclopropylmethyl-nicotinamide (Intermediate 21) | 368 | 2.78 |
| Example 33 6-(5-Cyclopropylcarbamoyl-3-fluoro-2-methyl-phenyl)-N-(3-methylbutyl)-nicotinamide | 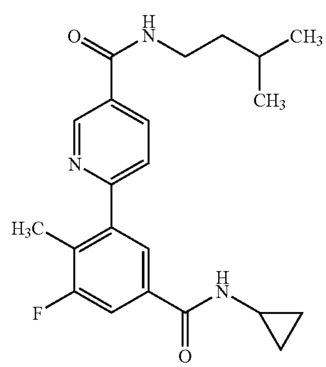 | 6-Chloro-N-(3-methylbutyl)nicotinamide (Intermediate 22) | 384 | 3.10 |
| Example 34 6-(5-Cyclopropylcarbamoyl-3-fluoro-2-methyl-phenyl)-N-cyclobutylmethyl-nicotinamide | 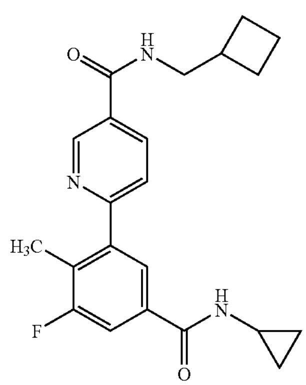 | 6-Chloro-N-cyclopropylmethyl-nicotinamide (Intermediate 32) | 382 | 3.01 |

-continued

| Compound | Structure | 6-Chloronicotinamide | MH+ | Retention time (minutes) |
|---|---|---|---|---|
| Example 35 6-(5-Cyclopropylcarbamoyl-3-fluoro-2-methyl-phenyl)-N-(1-cyclopropylethyl)-nicotinamide | 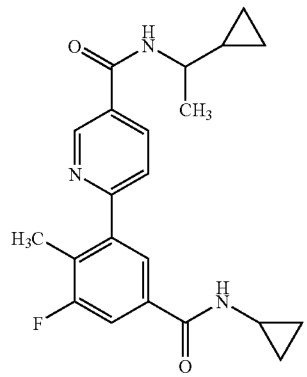 | 6-Chloro-N-(1-cyclopropylethyl)nicotinamide (Intermediate 23) | 382 | 2.95 |
| Example 36 6-(5-Cyclopropylcarbamoyl-3-fluoro-2-methyl-phenyl)-N-(2,2-dimethylpropyl)-nicotinamide | 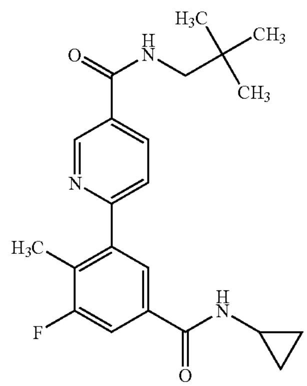 | 6-Chloro-N-(2,2-dimethylpropyl))nicotinamide (Intermediate 24) | 384 | 3.01 |
| Example 37 6-(5-Cyclopropylcarbamoyl-3-fluoro-2-methyl-phenyl)-N-(2,2-dimethylcyclopropyl)-nicotinamide | 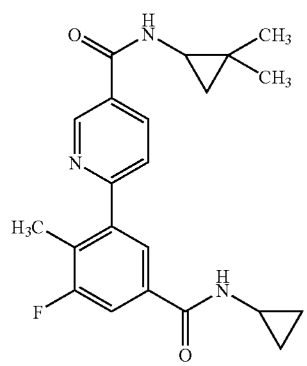 | 6-Chloro-N-(2,2-dimethylcyclopropyl)nicotinamide (Intermediate 25) | 382 | 2.90 |
| Example 38 6-(5-Cyclopropylcarbamoyl-3-fluoro-2-methyl-phenyl)-N-cyclopropyl-nicotinamide | 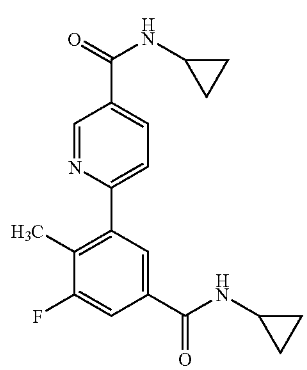 | 6-Chloro-N-cyclopropyl-nicotinamide (Intermediate 26) | 354 | 2.60 |

-continued

| Compound | Structure | 6-Chloronicotinamide | MH+ | Retention time (minutes) |
|---|---|---|---|---|
| Example 39 6-(5-Cyclopropylcarbamoyl-3-fluoro-2-methyl-phenyl)-N-cyclohexylmethyl-nicotinamide | 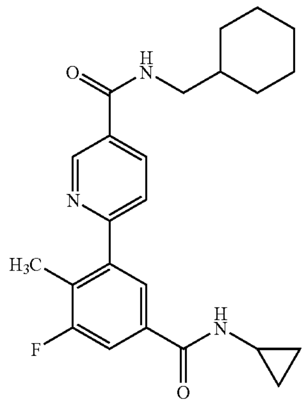 | 6-Chloro-N-cyclohexylmethyl-nicotinamide (Intermediate 27) | 410 | 3.22 |
| Example 40 6-(5-Cyclopropylcarbamoyl-3-fluoro-2-methyl-phenyl)-N-cyclobutyl-nicotinamide | 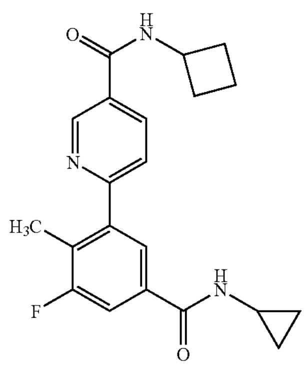 | 6-Chloro-N-cyclobutyl-nicotinamide (Intermediate 28) | 368 | 2.79 |
| Example 41 6-(5-Cyclopropylcarbamoyl-3-fluoro-2-methyl-phenyl)-N-(2-methylpropyl)-nicotinamide | 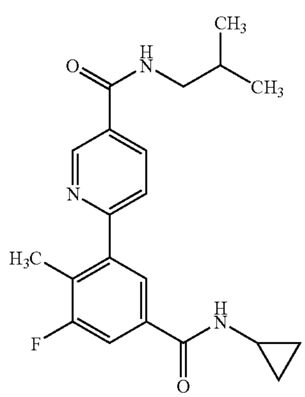 | 6-Chloro-N-(2-methylpropyl)nicotin-amide (Intermediate 29) | 370 | 2.86 |
| Example 42 6-(5-Cyclopropylcarbamoyl-3-fluoro-2-methyl-phenyl)-N-(1-methylpropyl)-nicotinamide | 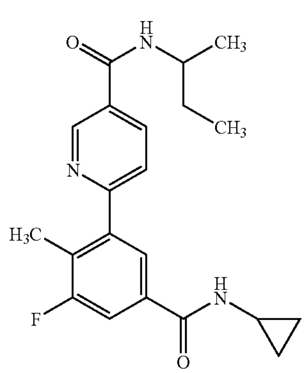 | 6-Chloro-N-(1-methylpropyl)nicotin-amide (Intermediate 33) | 370 | 2.84 |

| Compound | Structure | 6-Chloronicotinamide | MH+ | Retention time (minutes) |
|---|---|---|---|---|
| Example 43 6-(5-Cyclopropylcarbamoyl-3-fluoro-2-methyl-phenyl)-N-propyl-nicotinamide | 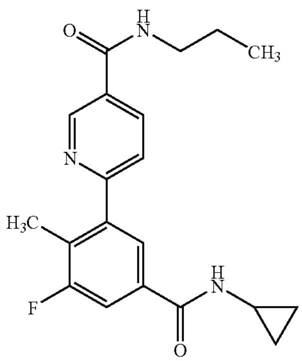 | 6-Chloro-N-propylnicotinamide (Intermediate 30) | 356 | 2.72 |
| Example 44 6-(5-Cyclopropylcarbamoyl-3-fluoro-2-methyl-phenyl)-N-cyclopentyl-nicotinamide | 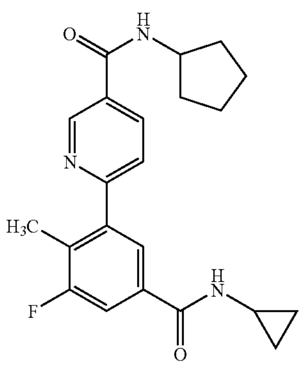 | 6-Chloro-N-cyclopentylnicotinamide (Intermediate 31) | 382 | 2.92 |

General Method D

Intermediate 38 (40 μmol) in DMF(0.5 ml) was treated with HATU (1.12 eq) and DIPEA (3 eq). On shaking a solution was formed which was added to a solution of amine (1.2-2.0 eq) in DMF (0.5 ml). After shaking the reactions were left overnight at room temperature. The solvent was removed in vacuo, the residue dissolved in chloroform (1.0 ml) and applied to an SPE (NH$_2$, 0.5 g). The product was eluted with chloroform (1.5 ml), ethyl acetate (1.5 ml) and methanol/ethyl acetate (1:9, 1.5 ml). The solvent was evaporated under vacuum from the product fraction.

| Compound | Amine | MH+ | Retention time (minutes) |
|---|---|---|---|
| Example 45 6-{5-[(cyclopropylamino)carbonyl]-3-fluoro-2-methylphenyl}-N-(1,3-thiazol-2-ylmethyl)nicotinamide | 2-aminomethylthiazole | 411 | 2.79 |
| Example 46 6-{5-[(cyclopropylamino)carbonyl]-3-fluoro-2-methylphenyl}-N-[2-(1,3-thiazol-2-yl)ethyl]nicotinamide | 2-(2-aminoethyl)thiazole | 425 | 2.78 |
| Example 47 6-{5-[(cyclopropylamino)carbonyl]-3-fluoro-2-methylphenyl}-N-(2-methylbenzyl)nicotinamide | 2-methylbenzylamine | 418 | 3.26 |

-continued

| Compound | Amine | MH+ | Retention time (minutes) |
|---|---|---|---|
| Example 48 6-{5-[(cyclopropylamino)carbonyl]-3-fluoro-2-methylphenyl}-N-(2,4,5-trifluorobenzyl)nicotinamide | 2,4,5-trifluorobenzylamine | 458 | 3.29 |
| Example 49 6-{5-[(cyclopropylamino)carbonyl]-3-fluoro-2-methylphenyl}-N-(2,5-difluorobenzyl)nicotinamide | 2,5-difluorobenzylamine | 440 | 3.21 |
| Example 50 6-{5-[(cyclopropylamino)carbonyl]-3-fluoro-2-methylphenyl}-N-(3,4-difluorobenzyl)nicotinamide | 3,4-difluorobenzylamine | 440 | 3.24 |
| Example 51 N-(3-chlorobenzyl)-6-{5-[(cyclopropylamino)carbonyl]-3-fluoro-2-methylphenyl}nicotinamide | 3-chlorobenzylamine | 438 | 3.33 |
| Example 52 N-(4-chlorobenzyl)-6-{5-[(cyclopropylamino)carbonyl]-3-fluoro-2-methylphenyl}nicotinamide | 4-chlorobenzylamine | 438 | 3.34 |
| Example 53 N-(3-chloro-2-fluorobenzyl)-6-{5-[(cyclopropylamino)carbonyl]-3-fluoro-2-methylphenyl}nicotinamide | 3-chloro-2-fluorobenzylamine | 456 | 3.36 |
| Example 54 6-{5-[(cyclopropylamino)carbonyl]-3-fluoro-2-methylphenyl}-N-(5-fluoro-2-methylbenzyl)nicotinamide | 5-fluoro-2-methylbenzylamine | 436 | 3.30 |
| Example 55 N-(2-chloro-3,6-difluorobenzyl)-6-{5-[(cyclopropylamino)carbonyl]-3-fluoro-2-methylphenyl}nicotinamide | 2-chloro-3,6-difluorobenzylamine | 474 | 3.31 |
| Example 56 6-{5-[(cyclopropylamino)carbonyl]-3-fluoro-2-methylphenyl}-N-(1-methylbutyl)nicotinamide | 2-pentylamine | 384 | 3.14 |
| Example 57 6-{5-[(cyclopropylamino)carbonyl]-3-fluoro-2-methylphenyl}-N-(2,3-difluoro-4-methylbenzyl)nicotinamide | 2,3-difluoro-4-methylbenzylamine | 454 | 3.36 |
| Example 58 6-{5-[(cyclopropylamino)carbonyl]-3-fluoro-2-methylphenyl}-N-(2,3,5-trifluorobenzyl)nicotinamide | 2,3,6-trifluorobenzylamine | 458 | 3.29 |
| Example 59 6-{5-[(cyclopropylamino)carbonyl]-3-fluoro-2-methylphenyl}-N-(1,3-dimethylbutyl)nicotinamide | 1,3-dimethylbutylamine | 398 | 3.28 |

| Compound | Amine | MH+ | Retention time (minutes) |
|---|---|---|---|
| Example 60<br>6-{5-[(cyclopropylamino)carbonyl]-3-fluoro-2-methylphenyl}-N-(3-fluoro-4-methylbenzyl)nicotinamide | 3-fluoro-4-methylbenzylamine | 436 | 3.32 |
| Example 61<br>N-(5-chloro-2-fluorobenzyl)-6-{5-[(cyclopropylamino)carbonyl]-3-fluoro-2-methylphenyl}nicotinamide | 5-chloro-2-fluorobenzylamine | 456 | 3.36 |
| Example 62<br>6-{5-[(cyclopropylamino)carbonyl]-3-fluoro-2-methylphenyl}-N-(2-phenylethyl)nicotinamide | 2-phenylethylamine | 418 | 3.20 |
| Example 63<br>6-{5-[(cyclopropylamino)carbonyl]-3-fluoro-2-methylphenyl}-N-(2-methoxy-2-methylpropyl)nicotinamide | 2-methoxy-2-methylpropylamine | 400 | 2.79 |
| Example 64<br>6-{5-[(cyclopropylamino)carbonyl]-3-fluoro-2-methylphenyl}-N-(2-methoxyethyl)nicotinamide | 2-methoxyethylamine | 372 | 2.63 |
| Example 65<br>6-{5-[(cyclopropylamino)carbonyl]-3-fluoro-2-methylphenyl}-N-(3,3-dimethylbutyl)nicotinamide | 3,3-dimethylbutylamine | 398 | 3.30 |
| Example 66<br>N-(2-tert-butoxyethyl)-6-{5-[(cyclopropylamino)carbonyl]-3-fluoro-2-methylphenyl}nicotinamide | 2-t-butoxyethylamine | 414 | 2.98 |
| Example 67<br>6-{5-[(cyclopropylamino)carbonyl]-3-fluoro-2-methylphenyl}-N-(tert-pentyl)nicotinamide | 1,1-dimethylpropylamine | 384 | 3.17 |
| Example 68<br>6-{5-[(cyclopropylamino)carbonyl]-3-fluoro-2-methylphenyl}-N-[(4-methyl-1,3-thiazol-2-yl)methyl]nicotinamide | 2-(aminomethyl)-4-methylthiazole | 425 | 2.88 |
| Example 69<br>6-{5-[(cyclopropylamino)carbonyl]-3-fluoro-2-methylphenyl}-N-(2-hydroxy-1,1-dimethylpentyl)nicotinamide | 1,1-dimethyl-2-hydroxypentylamine | 428 | 3.08 |
| Example 70<br>6-{5-[(cyclopropylamino)carbonyl]-3-fluoro-2-methylphenyl}-N-[2-(trifluoromethyl)benzyl]nicotinamide | 2-trifluoromethylbenzylamine | 472 | 3.38 |
| Example 71<br>N-(2-chlorobenzyl)-6-{5-[(cyclopropylamino)carbonyl]-3-fluoro-2-methylphenyl}nicotinamide | 2-chlorobenzylamine | 438 | 3.30 |

-continued

| Compound | Amine | MH+ | Retention time (minutes) |
|---|---|---|---|
| Example 72 N-cyclopropyl-3-fluoro-4-methyl-5-{5-[(4-methylpiperidin-1-yl)carbonyl]pyridin-2-yl}benzamide | 4-methylpiperidine | 396 | 3.09 |
| Example 73 6-{5-[(cyclopropylamino)carbonyl]-3-fluoro-2-methylphenyl}-N-isobutyl-N-methylnicotinamide | N-isobutyl-N-methylamine | 384 | 3.02 |
| Example 74 6-{5-[(cyclopropylamino)carbonyl]-3-fluoro-2-methylphenyl}-N-(4-fluorobenzyl)nicotinamide | 4-fluorobenzylamine | 422 | 3.19 |
| Example 75 N-cyclopropyl-3-{5-[(3,3-diethylazetidin-1-yl)carbonyl]pyridin-2-yl}-5-fluoro-4-methylbenzamide | 3,3-diethylazetidine | 410 | 3.24 |
| Example 76 N-cyclopentyl-6-{5-[(cyclopropylamino)carbonyl]-3-fluoro-2-methylphenyl}-N-methylnicotinamide | N-cyclopropyl-N-methylamine | 396 | 3.06 |
| Example 77 6-{5-[(cyclopropylamino)carbonyl]-3-fluoro-2-methylphenyl}-N-ethyl-N-isopropylnicotinamide | N-ethyl-N-isopropylamine | 384 | 2.98 |
| Example 78 6-{5-[(cyclopropylamino)carbonyl]-3-fluoro-2-methylphenyl}-N-(2,3,4-trifluorobenzyl)nicotinamide | 2,3,4-trifluorobenzylamine | 458 | 3.30 |
| Example 79 N-benzyl-6-{5-[(cyclopropylamino)carbonyl]-3-fluoro-2-methylphenyl}nicotinamide | benzylamine | 404 | 3.14 |
| Example 80 N-cyclopropyl-3-{5-[(2-ethylpiperidin-1-yl)carbonyl]pyridin-2-yl}-5-fluoro-4-methylbenzamide | 2-ethylpiperidine | 410 | 3.17 |
| Example 81 6-{5-[(cyclopropylamino)carbonyl]-3-fluoro-2-methylphenyl}-N-[3-(trifluoromethyl)benzyl]nicotinamide | 3-trifluoromethylbenzylamine | 472 | 3.40 |
| Example 82 N-cyclopropyl-3-{5-[(2-ethyl-2-methylpiperidin-1-yl)carbonyl]pyridin-2-yl}-5-fluoro-4-methylbenzamide | 2-ethyl-2-methylpiperidine | 424 | 3.30 |
| Example 83 6-{5-[(cyclopropylamino)carbonyl]-3-fluoro-2-methylphenyl}-N-(1,1-dimethylbutyl)nicotinamide | 1,1-dimethylbutylamine | 398 | 3.30 |
| Example 84 N-(4-chloro-2-fluorobenzyl)-6-{5-[(cyclopropylamino)carbonyl]-3-fluoro-2-methylphenyl}nicotinamide | 4-chloro-2-fluorobenzylamine | 456 | 3.37 |

| Compound | Amine | MH+ | Retention time (minutes) |
|---|---|---|---|
| Example 85<br>6-{5-[(cyclopropylamino)carbonyl]-3-fluoro-2-methylphenyl}-N-(3,3,3-trifluoropropyl)nicotinamide | 3,3,3-trifluoropropylamine | 410 | 3.00 |
| Example 86<br>6-{5-[(cyclopropylamino)carbonyl]-3-fluoro-2-methylphenyl}-N-[4-(trifluoromethyl)benzyl]nicotinamide | 4-trifluoromethylbenzylamine | 472 | 3.41 |
| Example 87<br>6-{5-[(cyclopropylamino)carbonyl]-3-fluoro-2-methylphenyl}-N-(3-methoxyphenyl)nicotinamide | 3-methoxyaniline | 420 | 3.26 |
| Example 88<br>6-{5-[(cyclopropylamino)carbonyl]-3-fluoro-2-methylphenyl}-N-(4-methylphenyl)nicotinamide | 4-methylaniline | 404 | 3.34 |
| Example 89<br>6-{5-[(cyclopropylamino)carbonyl]-3-fluoro-2-methylphenyl}-N-(3-fluorobenzyl)nicotinamide | 3-fluorobenzylamine | 422 | 3.20 |
| Example 90<br>6-{5-[(cyclopropylamino)carbonyl]-3-fluoro-2-methylphenyl}-N-[(5-methyl-2-furyl)methyl]nicotinamide | 2-aminomethyl-5-methylfuran | 408 | 3.09 |
| Example 91<br>6-{5-[(cyclopropylamino)carbonyl]-3-fluoro-2-methylphenyl}-N-(3-methylphenyl)nicotinamide | 3-methylaniline | 404 | 3.36 |
| Example 92<br>6-{5-[(cyclopropylamino)carbonyl]-3-fluoro-2-methylphenyl}-N-(2,3-difluorobenzyl)nicotinamide | 2,3-difluorobenzylamine | 440 | 3.23 |
| Example 93<br>6-{5-[(cyclopropylamino)carbonyl]-3-fluoro-2-methylphenyl}-N-(2,4-difluorobenzyl)nicotinamide | 2,4-difluorobenzylamine | 440 | 3.23 |
| Example 94<br>N-(3-chloro-4-fluorobenzyl)-6-{5-[(cyclopropylamino)carbonyl]-3-fluoro-2-methylphenyl}nicotinamide | 3-chloro-4-fluorobenzylamine | 456 | 3.37 |
| Example 95<br>6-{5-[(cyclopropylamino)carbonyl]-3-fluoro-2-methylphenyl}-N-(4-methylbenzyl)nicotinamide | 4-methylbenzylamine | 418 | 3.27 |
| Example 96<br>6-{5-[(cyclopropylamino)carbonyl]-3-fluoro-2-methylphenyl}-N-(3,4,5-trifluorobenzyl)nicotinamide | 3,4,5-trifluorobenzylamine | 458 | 3.33 |

-continued

| Compound | Amine | MH⁺ | Retention time (minutes) |
|---|---|---|---|
| Example 97 6-{5-[(cyclopropylamino)carbonyl]-3-fluoro-2-methylphenyl}-N-[(3-methylthien-2-yl)methyl]nicotinamide | 2-aminomethyl-3-methylthiophene | 424 | 3.21 |
| Example 98 N-(3-chloro-2,6-difluorobenzyl)-6-{5-[(cyclopropylamino)carbonyl]-3-fluoro-2-methylphenyl}nicotinamide | 3-chloro-2,6-difluorobenzylamine | 474 | 3.35 |
| Example 99 6-{5-[(cyclopropylamino)carbonyl]-3-fluoro-2-methylphenyl}-N-[(2-ethylcyclopropyl)methyl]nicotinamide | (2-ethylcyclopropyl)methylamine (Intermediate 39) | 396 | 3.24 |
| Example 100 N-cyclopropyl-3-fluoro-4-methyl-5-{[2-propylpiperidin-1-yl)carbonyl]pyridin-2-yl}benzamide | 2-propylpiperidine | 424 | 3.33 |
| Example 101 6-{5-[(cyclopropylamino)carbonyl]-3-fluoro-2-methylphenyl}-N-[2-(4-methyl-1,3-thiazol-2-yl)ethyl]nicotinamide | 2-(2-aminoethyl)-4-methylthiazole | 439 | 2.65 |
| Example 102 6-{5-[(cyclopropylamino)carbonyl]-3-fluoro-2-methylphenyl}-N-(2-fluoro-2-phenylethyl)nicotinamide | 2-fluoro-2-phenylethylamine | 436 | 3.07 |
| Example 103 6-{5-[(cyclopropylamino)carbonyl]-3-fluoro-2-methylphenyl}-N-[1-methyl-2-(1,3-thiazol-2-yl)ethyl]nicotinamide | 2-(2-aminopropyl)thiazole | 439 | 2.70 |
| Example 104 N-cyclopropyl-3-{5-[(2,4-dimethylpiperidin-1-yl)carbonyl]pyridin-2-yl}-5-fluoro-4-methylbenzamide | 2,4-dimethylpiperidine | 410 | 3.07 |
| Example 105 N-cyclopropyl-3-{5-[(2,3-dimethylpiperidin-1-yl)carbonyl]pyridin-2-yl}-5-fluoro-4-methylbenzamide | 2,3-dimethylpiperidine | 410 | 3.02 |
| Example 106 6-{5-[(cyclopropylamino)carbonyl]-3-fluoro-2-methylphenyl}-N-(3-methylbut-2-enyl)nicotinamide | 3-methylbut-2-enylamine | 382 | 2.97 |
| Example 107 6-{5-[(cyclopropylamino)carbonyl]-3-fluoro-2-methylphenyl}-N-methyl-N-(1-methylcyclopentyl)nicotinamide | N-methyl-N-(1-methylcyclopentyl)amine | 410 | 3.14 |
| Example 108 N-(2-cyclopentylethyl)-6-{5-[(cyclopropylamino)carbonyl]-3-fluoro-2-methylphenyl}-N-methylnicotinamide | N-(2-cyclopentylethyl)-N-methylamine | 424 | 3.26 |

-continued

| Compound | Amine | MH+ | Retention time (minutes) |
|---|---|---|---|
| Example 109<br>6-{5-[(cyclopropylamino)carbonyl]-3-fluoro-2-methylphenyl}-N-[(2E)-1,1-dimethylbut-2-enyl]nicotinamide | 1,1-dimethylbut-2-enylamine | 396 | 3.06 |
| Example 110<br>N-cyclopropyl-3-fluoro-4-methyl-5-{5-[(2,2,3-trimethylpyrrolidin-1-yl)carbonyl]pyridin-2-yl}benzamide | 2,2-dimethyl-3-methyl-pyrrolidine | 410 | 3.07 |
| Example 111<br>N-cyclopropyl-3-{5-[(3-ethylpiperidin-1-yl)carbonyl]pyridin-2-yl}-5-fluoro-4-methylbenzamide | 3-ethylpiperidine | 410 | 3.10 |
| Example 112<br>6-{5-[(cyclopropylamino)carbonyl]-3-fluoro-2-methylphenyl}-N-(3,3,3-trifluoro-2-methylpropyl)nicotinamide | 2-methyl-3,3,3,-trifluoropropylamine | 424 | 3.00 |
| Example 113<br>6-{5-[(cyclopropylamino)carbonyl]-3-fluoro-2-methylphenyl}-N-(1-ethyl-1-methylpropyl)nicotinamide | 1-ethyl-1-methylpropylamine | 398 | 3.15 |
| Example 114<br>N-cyclopropyl-3-fluoro-4-methyl-5-{5-[(2-methylpiperidin-1-yl)carbonyl]pyridin-2-yl}benzamide | 2-methylpiperidine | 396 | 2.90 |
| Example 115<br>N-cyclopropyl-3-{5-[(3,3-dimethylpiperidin-1-yl)carbonyl]pyridin-2-yl}-5-fluoro-4-methylbenzamide | 3,3,-dimethylpiperidine | 410 | 3.04 |
| Example 116<br>N-cyclopropyl-3-fluoro-4-methyl-5-{5-[(3-methylpiperidin-1-yl)carbonyl]pyridin-2-yl}benzamide | 3-methylpiperidine | 396 | 2.95 |
| Example 117<br>N-cyclohexyl-6-{5-[(cyclopropylamino)carbonyl]-3-fluoro-2-methylphenyl}-N-ethylnicotinamide | N-cyclohexyl-N-ethylamine | 424 | 3.18 |
| Example 118<br>6-{5-[(cyclopropylamino)carbonyl]-3-fluoro-2-methylphenyl}-N-ethylnicotinamide | ethylamine | 342 | 2.58 |
| Example 119<br>6-{5-[(cyclopropylamino)carbonyl]-3-fluoro-2-methylphenyl}-N-isopropyl-N-methylnicotinamide | N-isopropyl-N-methylamine | 370 | 2.72 |
| Example 120<br>6-{5-[(cyclopropylamino)carbonyl]-3-fluoro-2-methylphenyl}-N-(2-hydroxy-1-methylpentyl)nicotinamide | 3-hydroxy-1-methylpentylamine | 414 | 2.88 |

-continued

| Compound | Amine | MH+ | Retention time (minutes) |
|---|---|---|---|
| Example 121<br>6-{5-[(cyclopropylamino)carbonyl]-3-fluoro-2-methylphenyl}-N-(2-fluorobenzyl)nicotinamide | 2-fluorobenzylamine | 422 | 3.18 |
| Example 122<br>6-{5-[(cyclopropylamino)carbonyl]-3-fluoro-2-methylphenyl}-N-(3-methylbenzyl)nicotinamide | 3-methylbenzylamine | 418 | 3.27 |
| Example 123<br>N-(cyclopentylmethyl)-6-{5-[(cyclopropylamino)carbonyl]-3-fluoro-2-methylphenyl}nicotinamide | cyclopentylmethylamine | 396 | 3.23 |

Abbreviations
DCM Dichloromethane
DIPEA N,N-Diisopropylethylamine
DME Dimethoxyethane
DMF Dimethylformamide
DMSO Dimethylsulphoxide
HATU O-(7-Azabenzotriazol-1-yl)-N,N,N',N'-tetramethyluronium hexafluorophosphate
HOBT 1-Hydroxybenzotriazole hydrate
SPE bond-elut (solid phase extraction column)

The activity of the compounds of the invention as p38 inhibitors may be demonstrated in the following assays:

p38 Kinase Assay

The peptide substrate used in the p38 assay was biotin-IPTSPITTTYFFFRRR-amide. The p38 and MEK6 proteins were purified to homogeneity from *E. coli* expression systems. The fusion proteins were tagged at the N-terminus with Glutathione-S-Transferase (GST). The maximum activation was achieved by incubating 20 uL of a reaction mixture of 30 nM MEK6 protein and 120 nM p38 protein in the presence of 1.5 uM peptide and 10 mM Mg(CH$_3$CO$_2$)$_2$ in 100 mM HEPES, pH 7.5, added to 15 uL of a mixture of 1.5 uM ATP with 0.08 uCi [g-$^{33}$P]ATP, with or without 15 uL of inhibitor in 6% DMSO. The controls were reactions in the presence (negative controls) or absence (positive controls) of 50 mM EDTA. Reactions were allowed to proceed for 60 min at room temperature and quenched with addition of 50 uL of 250 mM EDTA and mixed with 150 uL of Streptavidin SPA beads (Amersham) to 0.5 mg/reaction. The Dynatech Microfluor white U-bottom plates were sealed and the beads were allowed to settle overnight. The plates were counted in a Packard TopCount for 60 seconds. IC$_{50}$ values were obtained by fitting raw data to % I=100*(1-(I-C2)/(C1-C2)), where I was CPM of background, C1 was positive control, and C2 was negative control.

α P38 Fluorescence Polarisation Method

α P38 was prepared in house. SB4777790-R Ligand was diluted in HEPES containing MgCl$_2$, CHAPS, DTT and DMSO. This was added to blank wells of a Black NUNC 384 well plate. α P38 was added to this ligand mixture then added to the remainder of the 384 well plate containing controls and compounds. The plates were read on an LJL Analyst and Fluorescence Anisotropy used to calculate the compound inhibition.

Results

The compounds described in the Examples were tested as described above and had IC$_{50}$ values of <10 μM.

What is claimed is:

1. The compound which is 6-(5-cyclopropylcarbamoyl-3-fluoro-2-methyl-phenyl)-N-(2,2-dimethylpropyl)-nicotinamide, or a pharmaceutically acceptable salt thereof.

2. A pharmaceutical composition comprising 6-(5-cyclopropylcarbamoyl -3-fluoro-2-methyl-phenyl)-N-(2,2-dimethylpropyl)-nicotinamide, or a pharmaceutically acceptable salt thereof and a pharmaceutically acceptable carrier, diluent or excipient.

* * * * *